US012773293B2

(12) United States Patent
Vayser et al.

(10) Patent No.: US 12,773,293 B2
(45) Date of Patent: Oct. 27, 2026

(54) METHODS AND APPARATUS FOR CONTROLLING OPTICAL PROPERTIES OF LIGHT

(71) Applicant: Invuity, Inc., San Francisco, CA (US)

(72) Inventors: Alex Vayser, Mission Viejo, CA (US); Fernando Erismann, New York, NY (US); Douglas Rimer, Los Altos Hills, CA (US); Gaston Tudury, San Francisco, CA (US)

(73) Assignee: Stryker Corporation, Portage, MI (US)

( * ) Notice: Subject to any disclaimer, the term of this patent is extended or adjusted under 35 U.S.C. 154(b) by 900 days.

(21) Appl. No.: 17/540,312

(22) Filed: Dec. 2, 2021

(65) Prior Publication Data

US 2022/0087771 A1 Mar. 24, 2022

Related U.S. Application Data

(60) Continuation of application No. 16/122,051, filed on Sep. 5, 2018, now Pat. No. 11,229,499, which is a (Continued)

(51) Int. Cl.

| | |
|---|---|
| ***A61B 90/30*** | (2016.01) |
| *A61B 17/00* | (2006.01) |
| *A61B 17/02* | (2006.01) |

(52) U.S. Cl.

CPC .... *A61B 90/30* (2016.02); *A61B 2017/00946* (2013.01); *A61B 17/02* (2013.01); *A61B 2090/306* (2016.02)

(58) Field of Classification Search

CPC ..... A61B 17/02; A61B 90/30; A61B 19/5202; F21V 7/0091; F21V 7/22

See application file for complete search history.

(56) References Cited

U.S. PATENT DOCUMENTS

| | | |
|---|---|---|
| 3,638,644 A | 2/1972 | Reick |
| 3,641,332 A | 2/1972 | Reick et al. |

(Continued)

FOREIGN PATENT DOCUMENTS

| | | |
|---|---|---|
| CN | 102164621 A | 8/2001 |
| CN | 101373241 A | 2/2009 |

(Continued)

OTHER PUBLICATIONS

Controlling. (n.d.) Dictionary.com Unabridged. Retrieved Jun. 26, 2017 from Dictionary.com website http://www.dictionary.com/browse/controlling.

(Continued)

*Primary Examiner* — Eduardo C Robert
*Assistant Examiner* — Steven J Cotroneo
(74) *Attorney, Agent, or Firm* — McDonnell Boehnen Hulbert & Berghoff LLP

(57) ABSTRACT

A surgical instrument for illuminating a surgical field has an optical waveguide for transmitting light by total internal reflection. One or more control elements are disposed on the optical waveguide. The control elements extract light from the optical waveguide and control first and second optical properties of the extracted light Another surgical instrument includes a first and second optical waveguide for transmitting light by total internal reflection. A coupling element is attached to both optical waveguides such that the optical waveguides are movable and pivotable relative to one another.

24 Claims, 28 Drawing Sheets

Related U.S. Application Data division of application No. 14/035,583, filed on Sep. 24, 2013, now abandoned.

(60) Provisional application No. 61/705,027, filed on Sep. 24, 2012.

(56) References Cited

U.S. PATENT DOCUMENTS

| | | | | |
|---|---|---|---|---|
| 3,890,960 | A | 6/1975 | Wunsch et al. | |
| 4,226,228 | A | 10/1980 | Shin et al. | |
| 4,562,832 | A | 1/1986 | Wilder et al. | |
| 4,571,022 | A | 2/1986 | Lama et al. | |
| 4,592,344 | A | 6/1986 | Scheer | |
| 4,597,030 | A * | 6/1986 | Brody | A61B 1/07 385/115 |
| 4,605,990 | A | 8/1986 | Wilder et al. | |
| 4,643,172 | A | 2/1987 | Taff et al. | |
| 4,697,578 | A | 10/1987 | Burgin | |
| 4,807,599 | A | 2/1989 | Robinson et al. | |
| 4,842,356 | A | 6/1989 | Mori | |
| 4,952,022 | A * | 8/1990 | Genovese | G02B 6/0008 355/1 |
| 4,961,617 | A | 10/1990 | Shahidi et al. | |
| 5,035,232 | A | 7/1991 | Lutze et al. | |
| 5,138,678 | A | 8/1992 | Briggs et al. | |
| 5,343,330 | A | 8/1994 | Hoffman et al. | |
| 5,353,786 | A | 10/1994 | Wilk et al. | |
| 5,630,809 | A | 5/1997 | Connor | |
| 5,953,477 | A | 9/1999 | Wach et al. | |
| 6,031,958 | A | 2/2000 | McGaffigan | |
| 6,088,540 | A | 7/2000 | Leidig et al. | |
| 6,185,356 | B1 | 2/2001 | Parker et al. | |
| 6,347,874 | B1 | 2/2002 | Boyd et al. | |
| 6,379,016 | B1 | 4/2002 | Boyd et al. | |
| 6,411,373 | B1 | 6/2002 | Garside et al. | |
| 6,504,985 | B2 | 1/2003 | Parker et al. | |
| 6,846,089 | B2 | 1/2005 | Stevenson et al. | |
| 7,306,559 | B2 | 12/2007 | Williams | |
| 7,454,103 | B2 | 11/2008 | Olivier | |
| 7,486,854 | B2 | 2/2009 | Van Ostrand et al. | |
| 7,991,257 | B1 | 8/2011 | Coleman | |
| 8,033,706 | B1 | 10/2011 | Kelly et al. | |
| 8,111,968 | B2 | 2/2012 | Chakmakjian et al. | |
| 8,864,662 | B2 | 10/2014 | Grey et al. | |
| 9,510,848 | B2 | 12/2016 | Auld et al. | |
| 9,817,191 | B2 | 11/2017 | Kopp et al. | |
| 2002/0009275 | A1* | 1/2002 | Williams | G02B 6/0008 385/901 |
| 2003/0095781 | A1 | 5/2003 | Williams | |
| 2004/0047162 | A1 | 3/2004 | Saccomanno et al. | |
| 2005/0113641 | A1 | 5/2005 | Bala | |
| 2006/0237735 | A1 | 10/2006 | Naulin et al. | |
| 2006/0268570 | A1 | 11/2006 | Vayser et al. | |
| 2007/0189701 | A1 | 8/2007 | Chakmakjian et al. | |
| 2007/0208226 | A1 | 9/2007 | Grey et al. | |
| 2007/0265602 | A1 | 11/2007 | Mordaunt et al. | |
| 2007/0270653 | A1 | 11/2007 | Vayser et al. | |
| 2008/0002426 | A1* | 1/2008 | Vayser | A61C 1/088 362/574 |
| 2009/0036744 | A1 | 2/2009 | Vayser | |
| 2009/0052840 | A1 | 2/2009 | Kojima et al. | |
| 2009/0112068 | A1 | 4/2009 | Grey et al. | |
| 2009/0244690 | A1 | 10/2009 | Lee | |
| 2010/0041955 | A1* | 2/2010 | Grey | A61L 29/041 600/212 |
| 2010/0214786 | A1 | 8/2010 | Nichol | |
| 2010/0309687 | A1 | 12/2010 | Sampsell et al. | |
| 2011/0001431 | A1 | 1/2011 | Brukilacchio | |
| 2011/0001901 | A1 | 1/2011 | Solomon et al. | |
| 2011/0013420 | A1 | 1/2011 | Coleman et al. | |
| 2011/0112376 | A1* | 5/2011 | Vayser | A61M 1/84 600/249 |
| 2011/0176325 | A1 | 7/2011 | Sherman et al. | |
| 2011/0227487 | A1 | 9/2011 | Nichol et al. | |
| 2011/0255303 | A1* | 10/2011 | Nichol | G02B 6/0088 362/606 |
| 2011/0273906 | A1 | 11/2011 | Nichol et al. | |
| 2011/0277361 | A1 | 11/2011 | Nichol et al. | |
| 2012/0033443 | A1 | 2/2012 | Aho et al. | |
| 2012/0041268 | A1* | 2/2012 | Grey | A61B 1/267 600/199 |
| 2012/0116170 | A1 | 5/2012 | Vayser et al. | |
| 2012/0215073 | A1* | 8/2012 | Sherman | A61B 90/30 600/249 |
| 2013/0079598 | A1 | 3/2013 | Auld et al. | |
| 2013/0121005 | A1 | 5/2013 | Dahmen | |
| 2014/0221763 | A1 | 8/2014 | Vayser et al. | |
| 2019/0000587 | A1 | 1/2019 | Vayser et al. | |

FOREIGN PATENT DOCUMENTS

| | | | |
|---|---|---|---|
| EP | 0101781 | A1 | 3/1984 |
| EP | 2897516 | B1 | 12/2017 |
| GB | 2078526 | A | 1/1982 |
| JP | H05-224090 | | 9/1993 |
| WO | 2007033125 | A1 | 3/2007 |
| WO | 2007146314 | A2 | 12/2007 |
| WO | 2011032135 | A2 | 3/2011 |
| WO | 2011071728 | A1 | 6/2011 |
| WO | 2011148173 | A2 | 12/2011 |
| WO | 2012112454 | A2 | 8/2012 |
| WO | 2014047651 | A2 | 3/2014 |

OTHER PUBLICATIONS

European Search Report and Search Opinion dated Mar. 31, 2016 for EP Application No. 13839373.1.

International Search Report and Written Opinion dated Apr. 29, 2014 for PCT/US2013/061471.

Wu, et al. A concave photonic crystal waveguide with a corrugated surface for high-quality focusing. Chin. Opt. Lett., 2011, 09(01); pp. 011301, DOI:10.3788/COL201109.011301.

English Translation of Abstract of European Patent Application No. 0101781 dated Aug. 20, 2019.

* cited by examiner

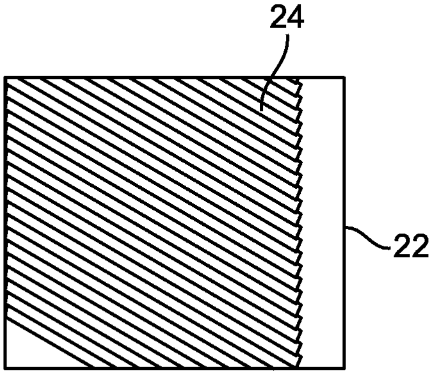
FIG. 2
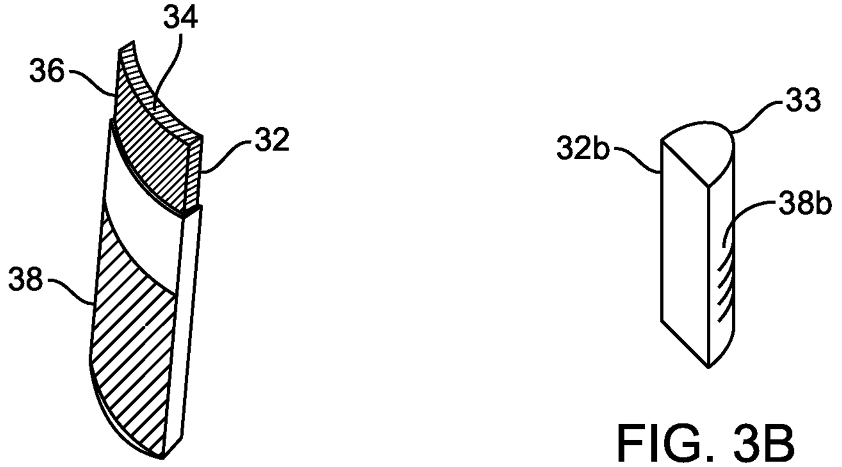
FIG. 3A
FIG. 3B
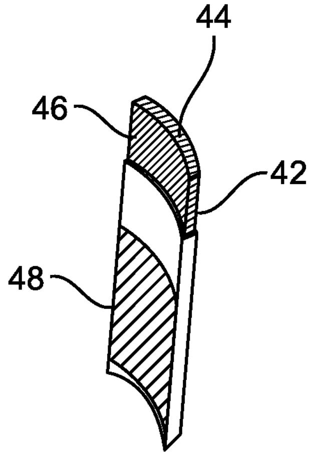
FIG. 4

METHODS AND APPARATUS FOR CONTROLLING OPTICAL PROPERTIES OF LIGHT

CROSS-REFERENCE

The present application is a continuation of U.S. patent application Ser. No. 16/122,051, filed Sep. 5, 2018, which is a divisional of U.S. patent application Ser. No. 14/035,583, filed Sep. 24, 2013, which claims the benefit of U.S. Provisional Patent Application 61/705,027, filed Sep. 24, 2012, each of which applications is entirely incorporated herein by reference.

BACKGROUND OF THE INVENTION

Illumination of target areas to allow an operator to more clearly observe the target area can be challenging. External lighting provided by headlamps or wall mounted lights require constant adjustment and can still cast unwanted shadows in the target area. Additionally, these methods of illumination may not be capable of illuminating a target area that is deep and disposed far below a surface. Fiber optics may be coupled to tools to help illuminate the target area, but fiber optic systems can be inefficient at transmitting light, and the resulting light loss significantly reduces the amount of light delivered to the target area. Attempts to overcome inefficiency of light transmission may be made by providing powerful light sources, but this can result in excessive heat generation and in some cases this results in fires. In addition to challenges associated with providing adequate illumination of the work area, the illumination system must be able to access tight spaces without occupying significant volume that otherwise is needed for tools, an operator's hands, or otherwise visualizing the working area. The illumination devices and systems must also be able to cooperatively interact with the tools being used and conform to the space in which they are being used.

Therefore, there still is a need for improved lighting devices and systems that efficiently deliver light and provide quality light to illuminate a work area. Such lighting devices and systems preferably have low profiles so they can be easily positioned in the work area and conform to the area without occupying too much space. In preferred embodiments, the lighting devices and systems may be used in surgical applications to illuminate a surgical field, and they may be used cooperatively with other surgical instruments such as retractors that keep tissue away from the working area or suction wands that remove unwanted fluids and debris from the surgical field. At least some of these objectives will be met by the exemplary embodiments described herein.

SUMMARY OF THE INVENTION

The present invention generally relates to instruments for illuminating an area, and preferably may relate to instruments for illuminating surgical fields.

In a first aspect of the present invention, a surgical instrument for illuminating a surgical field comprises an optical waveguide for transmitting light from a proximal end of the optical waveguide to a distal end of the optical waveguide by total internal reflection. The optical waveguide has a front surface and a rear surface. The surgical instrument also has one or more control elements disposed on the front surface and/or the rear surface that extract light from the optical waveguide and independently control two or more optical properties of the extracted light. The control elements may be surface features on the waveguide and thus may also be referred to in this specification as surface features. However, this is not intended to be limiting and thus the control elements need not be surface features.

The optical waveguide may be a non-fiber optic waveguide and may be formed from a single homogenous material. The one or more control elements may comprise a first surface feature disposed on the front surface and a second surface feature disposed on the rear surface. The two or more optical properties may comprise a first and second optical property. The first optical property may comprise a first direction or a first divergence angle, and the second optical property may comprise a second direction or a second divergence angle, and the first surface feature controls the extracted light in the first direction or the first divergence angle, and the second surface feature controls the extracted light in the second direction or the second divergence angle. The one or more control elements may comprise one or more front control elements disposed on the front surface and one or more rear control elements disposed on the rear surface. The front control elements may control the first optical property independently of the one or more rear control elements which control the second optical property. At least some of the one or more control elements may control both the first and the second optical property and they may be disposed on the front or rear or both surfaces. The first control element may be different than the second control element. The one or more control elements may comprise a prismatic pattern, a plurality of facets, or a lenticular lens.

The prismatic pattern may comprise a thickness, a riser and an exit face, and a groove having a depth that extends from a top of the riser to a bottom of the exit face. The groove depth may be less than ⅓ of the thickness of the optical waveguide. The groove depth may be constant along the prismatic pattern. The optical waveguide may comprise a plurality of grooves, and the plurality of grooves may fit an aspheric equation. The prismatic pattern may have a pitch of less than 1 mm, and the riser may have a riser angle of 0 degrees to 25 degrees. The exit face may have an exit face angle of 0 degrees to 25 degrees. The prismatic pattern may be orthogonal to the longitudinal axis of the optical waveguide.

The control elements may comprise a plurality of facets disposed on the front or rear surface. One or more control elements may comprise a lenticular lens that may be parallel to the longitudinal axis of the optical waveguide. The front surface of the optical waveguide may be substantially planar and the rear surface may comprise a concave or convex lenticular lens having a pitch and a radius. The pitch and radius may control lateral divergence of light extracted through the lens and relative to the longitudinal axis of the optical waveguide.

The optical waveguide may comprise a longitudinal axis and the first direction may be transverse to the longitudinal axis. The first optical property may comprise a first direction or a first divergence angle and the direction or first divergence angle may be transverse to the longitudinal axis. The first direction or first divergence angle may form an angle relative to the longitudinal axis. The second optical property may comprise a second direction or a second divergence angle and the second direction or second divergence angle may be transverse to the first direction. The second direction or second divergence angle may form a divergence angle relative to the longitudinal axis.

The one or more control elements may comprise a first group of surface features oriented parallel to the longitudinal axis of the optical waveguide for controlling light extraction in a direction transverse to the longitudinal axis, and a second group of surface features oriented transverse to the longitudinal axis for controlling light extraction in a direction that forms an angle relative to the longitudinal axis. The first group and the second group of surface features may be disposed on the same surface of the optical waveguide as one another. The one or more control elements may comprise surface features formed from a combination of features oriented in a first direction and a second direction opposite the first direction. The control elements may form one or more protuberances or pillows disposed on the front surface or the rear surface. The one or more protuberances control extracted light in the two directions or in the two divergence angles. The front or the rear surface of the optical waveguide may comprise a convex or a concave region for controlling divergence angle of the light extracted from the waveguide, and the other of the front or the rear surface may be substantially planar. The optical waveguide may comprise an angled distal tip for capturing remaining light that has not been extracted by the one or more surface features. The tip may be angled, flat, or have other configurations. Additionally, the tip may have surface features such as microfeatures including prisms, lenslets, facets, or other configurations for controlling the light exiting the distal tip of the optical waveguide. The one or more surface features may comprise surface features disposed on the front surface and surface features that are disposed on the rear surface. The surface features on the front may control the first optical property and the surface features on the rear may control the second optical property. A coating or cladding may be disposed over the front or rear surfaces. The coating or cladding may have an index of refraction that is lower than the index of refraction of the waveguide.

In another aspect of the present invention, a method for illuminating a surgical field comprises providing an optical waveguide having a front surface and a rear surface, inputting light into the optical waveguide, and transmitting the light through the optical waveguide by total internal reflection. The method also comprises extracting light from the optical waveguide via one or more control elements disposed on the front or rear surface of the optical waveguide, and controlling the extracted light from the optical waveguide controls at least two optical properties of the extracted light with the one or more surface features. The two optical properties may include two directions or two divergence angles so that the light illuminates the surgical field.

Inputting the light may comprise optically coupling the optical waveguide with a source of light. Optically coupling may comprise coupling the optical waveguide with a fiber optic. The one or more control elements may be disposed on only the front surface or only on the rear surface of the optical waveguide. Controlling the extracted light may comprise controlling horizontal and vertical divergence of the extracted light relative to the longitudinal axis of the optical waveguide.

In another aspect of the present invention, a surgical instrument for illuminating a surgical field comprises a first optical waveguide and a second optical waveguide. The waveguides are configured for transmitting light from a light source to the surgical field by total internal reflection, and the optical waveguides have a front surface facing the surgical field and a rear surface opposite thereto. The surgical instrument also comprises a coupling element attached to both the first optical waveguide and the second optical waveguide. The coupling element has a longitudinal axis, and the first and second optical waveguides are movable relative to one another and pivotable about the longitudinal axis.

The coupling element may allow positioning of the first optical waveguide relative to the second optical waveguide so that an angle or radius of curvature between the two optical waveguides is adjustable. The first optical waveguide or the second optical waveguide may comprise one or more control elements that are disposed on either the front surface or the rear surface, and the one or more control elements extract light from the optical waveguide and control a first optical property of the extracted light. The one or more control elements may also extract light from the optical waveguide and control a second optical property of the extracted light.

The surgical instrument may further comprise a retractor blade having an inner and outer surface, and that is coupled to the first optical waveguide or the second optical waveguide. The first and second optical waveguides may conform to the inner or the outer surface of the retractor blade or to any other substrate such as a malleable backing. The retractor blade may comprise a tubular cannula and the first or the second optical waveguide may comprise a planar and rectangular shaped waveguide. The first or the second optical waveguide may comprise a trapezoidal cross-section. Preferably, an air gap is disposed between the waveguides and the retractor blade or other substrate. The air gap helps prevent light loss and may be used in any of the embodiments described in this specification. Alternatively, a cladding or coating having an index of refraction lower than the waveguide may be disposed between the waveguides and the retractor blade or other substrate. The coating or cladding may also be used to help prevent light loss. In this embodiment, or any coating or cladding embodiments described in this specification, the index of refraction of the coating or cladding is preferably lower than the index of refraction of the waveguide. An exemplary range of the index of refraction is from about 1 to about 1.5.

The coupling element may comprise a hinge, a film, or a flexible joint. The front or the rear surface of the first or the second optical waveguide may be convex or concave. The surgical instrument may further comprise a substrate layer of material and the first and second optical waveguides may be attached to the substrate. The first and the second optical waveguides may be disposed in a layer of material. An air gap may be disposed between the substrate and the first or the second optical waveguide. Each of the first and the second optical waveguides may be independently coupled with a light source. A separate optical fiber may be coupled to each of the first and second optical waveguides. The surgical instrument may further comprise an optical coating or cladding disposed over the first or the second optical waveguide. The coating or cladding may have an index of refraction lower than that of the respective optical waveguide thereby enhancing total internal reflection therein. A film may be disposed over the first or the second optical waveguide. The film may have surface features for extracting and controlling the extracted light. The film may polarize the extracted light. The first optical waveguide may comprise control elements for extracting and controlling optical properties of the light, and the second optical waveguide may comprise control elements which extract and control optical properties of the light. The surgical instrument may further comprise a stabilizing element coupled to the optical waveguides and adapted to hold the optical waveguides in a desired shape. The first optical waveguide may be substantially planar and the second optical waveguide may be convex or concave. The first optical waveguide may have a size or shape different than the second optical waveguide. The surgical instrument may further comprise one or more optical fibers optically coupled with each optical waveguide for inputting light thereinto. The surgical instrument may also have a single integrally formed input stem optically coupled with each optical waveguide for inputting light thereinto.

In another aspect of the present invention, a method for illuminating a surgical field comprises providing a first optical waveguide having a front surface facing the surgical field, and a rear surface opposite thereto, and providing a second optical waveguide having a front surface facing the surgical field, and a rear surface opposite thereto. The first and second optical waveguides are coupled together with a coupling element. The method also includes the steps of actuating the first and second optical waveguides about the coupling element to adjust angle or radius of curvature between the optical waveguides, and illuminating the surgical field with light extracted from the optical waveguides.

The method may further comprise fixing the position of the first and second optical waveguides thereby fixing the angle or radius of curvature therebetween. The method may also comprise coupling the optical waveguide with a surgical retractor blade.

In still another aspect of the present invention, a flexible illuminated surgical instrument may comprise an optional malleable backing element having a proximal portion and a distal portion, a fiber optic bundle and a non-fiber optical waveguide. The backing element may be manipulated into a plurality of shapes, and the fiber optic bundle has a proximal region and a distal region. The fiber optic bundle is cylindrically shaped in the proximal region, and the fiber optical bundle is flat and planar in the distal region. The fiber optic bundle may be coupled to the malleable backing. The non-fiber optical waveguide is optically coupled with the fiber optic bundle and also is coupled with the malleable backing. As in other embodiments, an air gap may be disposed between the waveguide any the backing element, or claddings or coatings may be applied to the waveguide to prevent light loss.

The distal portion of the malleable backing element may comprise a hinged region such that the distal portion is more flexible than the proximal portion thereof. The hinged region may comprise a plurality of serrations disposed along the malleable backing element. The instrument may further comprise a strain relief disposed over the proximal region of the fiber optic bundle. The strain relief is adapted to reduce kinking thereof. The instrument may also comprise an optical connector optically coupled with the proximal region of the fiber optic bundle.

The instrument may further comprise a crimping element crimped around the fiber optic bundle thereby coupling the fiber optic bundle to the malleable backing element. A sleeve may be disposed over the distal region of the fiber optic bundle and also disposed over a proximal portion of the optical waveguide. The sleeve may couple the optical waveguide with the fiber optic bundle. The instrument may comprise a frame that is coupled to a distal portion of the malleable backing element. The optical waveguide may be disposed in the frame.

The malleable backing element may comprise a window disposed along the distal portion thereof. The window may be configured to receive a portion of the optical waveguide. A proximal portion of the optical waveguide may comprise a flanged region for engaging a portion of the malleable backing. Standoffs may be disposed between the malleable backing and the optical waveguide. The standoffs form an air gap therebetween for enhancing total internal reflection of light travelling through the optical waveguide. The optical waveguide may comprise surface features for extracting light therefrom and controlling direction of the extracted light. The optical waveguide may also comprise a coating or cladding for controlling optical properties of the waveguide. The index of refraction of the coating or cladding is preferably less than the index of refraction of the waveguide.

In yet another aspect of the present invention, a method for illuminating a work space comprises proving an optical waveguide coupled to a malleable backing element, forming the backing element into a desired shape, coupling the optical waveguide to a source of light, extracting light from the optical waveguide, and illuminating the work space. Forming the backing element may comprise bending the backing element.

In still another aspect of the present invention, a surgical illumination system for illuminating a surgical field comprises an optical waveguide for illuminating the surgical field with light and a plurality of optical fibers arranged into a fiber bundle. The optical waveguide comprises a light input end, and light is transmitted through the waveguide by total internal reflection. The fiber bundle is optically coupled to the light input end, and the plurality of fibers in the bundle preferably have a diameter of 750 μm, but may be other sizes. The plurality of optical fibers are arranged in the bundle such that adjacent fibers engage one another with an interstitial space disposed therebetween. The fibers may be a polymer or they may be glass.

The plurality of fibers may be arranged into a bundle having an outer perimeter that is hexagonally shaped. The plurality of fibers may consist of 19 fibers when having a diameter of 750 μm to form an approximately 3.5 mm diameter bundle. Every three adjacent fibers may form a triangle. The plurality of fibers may be arranged in three concentric layers of fibers, or they may be arranged into a plurality of linear rows of fibers. More fibers may be combined to form a larger size bundle.

An optical element may be disposed between the bundle and the light input end of the waveguide. The optical element may comprise a lens, optical coupling gel, a relay rod or hollow coated cones. The optical coupling element may comprise a body having a circular shape on one end, and a hexagonal shape on an opposite end. The bundle may be butt coupled to the light input end of the waveguide.

These and other aspects and advantages of the invention are evident in the description which follows and in the accompanying drawings.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2 illustrates exemplary horizontally oriented prismatic structures.

FIGS. 3A-4 illustrates an exemplary embodiment of contoured waveguides having prismatic structures.

DETAILED DESCRIPTION OF THE INVENTION

Figure 1A:
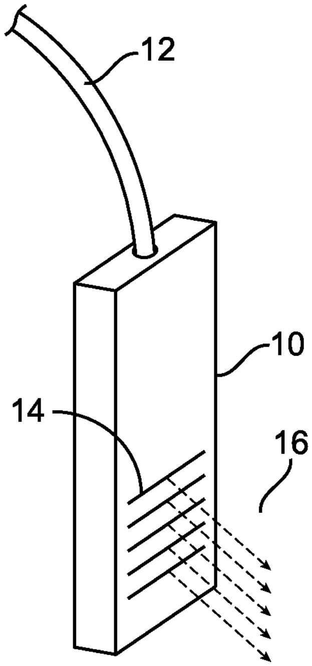
FIG. 1A illustrates extraction of light from an optical waveguide.
Figure 1B:
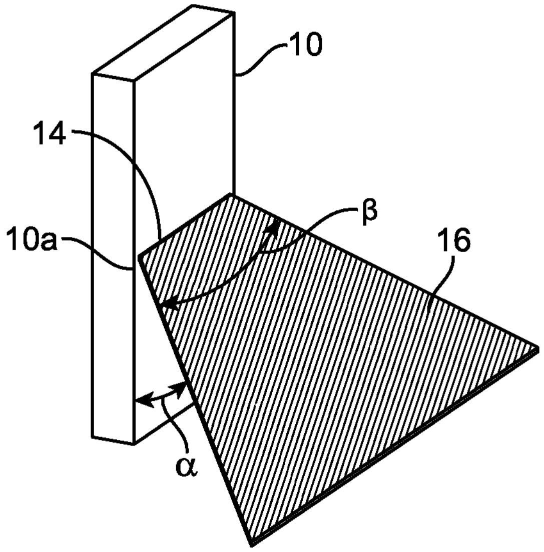
FIG. 1B illustrates light extraction directions and divergence angles relative to the waveguide.

Many illumination devices and systems provide little control of the light being outputted. For example, fiber optic cables typically only output light radially with a fixed angle from the distal fiber tip. Some optical waveguides deliver light more efficiently and can control light extraction and delivery more effectively such as the embodiment in FIG. 1A which illustrates extraction of light 16 from an optical waveguide 10. Light is input into the optical waveguide 10 typically with a fiber optic input 12 which can be coupled to an external light source. The waveguide includes prismatic surface features 14 on an outer surface of the waveguide. The prismatic surface features 14 extract light 16 from the waveguide 10 and direct the light 16 to a work area such as a surgical field or other target area. Prismatic surface features are described in greater detail in US Patent Publication Nos. 2009/0112068; 2009/0036744; 2008/0002426; 2007/0270653; 2007/0208226; and 2006/0268570; the entire contents of which are incorporated herein by reference. By controlling the angles and pitch of the prismatic structures 14 the amount of light extracted from the optical waveguide versus exiting the distal tip of the waveguide may be controlled. Additionally, the angle and pitch of the prismatic structures also controls the direction of the light extracted from the waveguide. FIG. 1B illustrates the angle α that the extracted light makes relative to the longitudinal axis 10*a* of the waveguide 10. Thus, the light is extracted and controlled vertically relative to the longitudinal axis of the waveguide. The light exiting the prismatic structures 14 in FIG. 1A will naturally diverge in the lateral or side-to-side direction. This direction may be referred to as horizontal relative to the longitudinal axis of the waveguide 10*a*, or lateral divergence and may be seen in FIG. 1B as angle β. While these optical waveguides are promising, they currently only extract the light from the optical waveguide and direct it toward the working area in one direction only. The light diverges naturally in the other directions. More effective illumination of a work area may be achieved by extracting the light and directing it in two directions. Preferably the light may be controlled both vertically as well as horizontally relative to the longitudinal axis of the optical waveguide, and even more preferably the light is controlled in two directions independently of one another. FIG. 1B illustrates light 16 exiting a waveguide 10 and highlights the vertical direction or angle α, as well as the horizontal or lateral divergence angle β of the light. Both directions or angles may be controlled with surface features on the waveguide to provide better lighting of a work field.

Providing a contoured optical waveguide with prismatic structures allow control of light extraction and direction in two directions. For example, FIG. 3A illustrates an optical waveguide 32 having a concave inner surface 34 and a convex outer surface 36. Horizontally oriented prisms like those in FIG. 1 extract and control light in a first direction that that is transverse to the longitudinal axis of the waveguide (also referred to as vertically relative to the longitudinal axis). The radius of curvature of the inner and outer surfaces of the optical waveguide may also be adjusted thereby controlling the lateral or side-to-side divergence of the light extracted from the waveguide (also referred to as horizontal direction or divergence relative to the longitudinal axis). Typically, the smaller the radius of curvature, the less divergence of light and similarly the larger the radius of curvature, the more the light will diverge. In FIG. 3A, the light will laterally diverge more than FIG. 1 because of the convex outer surface on which the prismatic structures 38 are disposed. FIG. 4 illustrates a similar embodiment of a contoured waveguide 42 except with the prismatic structures 48 disposed on the concave surface instead of the convex surface 44. Thus in FIG. 4, the extracted light will converge more than the embodiment of FIG. 1. Adjusting the shape or radius of the waveguide so that a convex or concave waveguide is created allows control of the light in two directions. FIG. 3B illustrates an alternative embodiment where the waveguide 32*b* is D-shaped and the horizontal prisms 38*b* are preferably disposed on the curved D-portion 33 of the waveguide. Thus, the prisms vertically control extracted light and the D-shape controls horizontal divergence. In other embodiments, the horizontal prisms may be disposed on the flat portion of the D-shape.

Contouring the waveguide may result in the formation of a single lenticular such as seen with the D-shaped waveguide in FIG. 3B. Multiple lenticulars further allow control of the light. Thus, in addition to contouring the waveguide to control the light, vertically oriented surface features such as vertical prisms or lenticulars may be used to control divergence of the light sideways. Thus, combining horizontal structures with vertical structures allows light to be extracted and controlled in two directions. The horizontal and vertical structures may be combined on one face of the waveguide, but this only has limited effect on side-to-side divergence. Thus, it is more effective to have horizontal structures on one surface of the waveguide and vertical structures on an opposite surface of the waveguide.

Figure 5A:
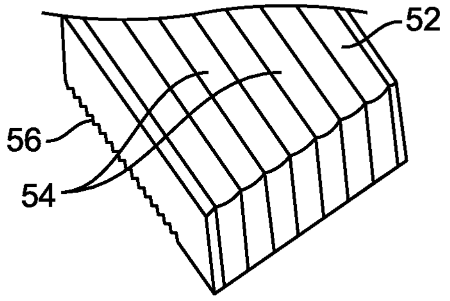
FIGS. 5A-5C illustrate an exemplary embodiment of a waveguide having prisms on one surface and lenticulars on an opposite surface.
Figure 5B:
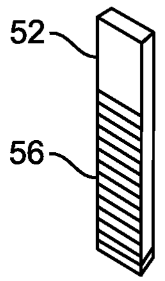
Figure 5C:
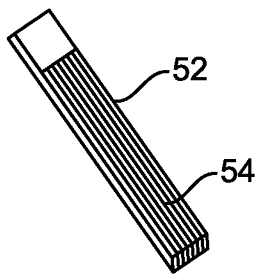

FIGS. 5A-5C illustrate an exemplary embodiment of an optical waveguide 52 having light extracting and controlling features on both the front and rear faces of the waveguide. FIG. 5A highlights the vertical lenticular features on the rear surface of the waveguide. Horizontal prismatic structures 56 are disposed on the front surface. Thus, the prismatic structures 56 extract and control the direction of the light vertically relative to the longitudinal axis of the waveguide, and the vertical lenticulars 54 control the side-to-side or horizontal divergence of the light. The vertical lenticulars may be convex or concave shaped. Preferably the vertical lenticulars are concave because they have the greatest effect on controlling sideways divergence of light. FIG. 5B more clearly illustrates the horizontal prisms 56 on the front surface of the waveguide 52 and FIG. 5C more clearly illustrates the lenticulars 54 on the rear surface of the waveguide 52.

Figure 6:
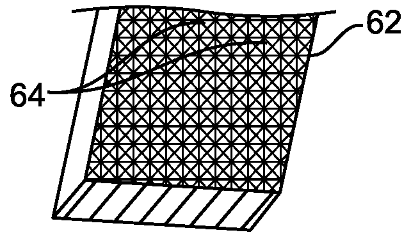
FIG. 6 illustrates an exemplary embodiment of a waveguide having pillow-like surface features.

FIG. 6 illustrates yet another exemplary embodiment of a waveguide for controlling extraction and direction of light in two directions. Waveguide 62 includes horizontally oriented and vertically oriented lenticulars 64 disposed preferably on a rear surface (or they may be disposed on a front surface) of the waveguide. The horizontal and vertical lenticulars form pincushion-like protuberances for controlling the extracted light. The pincushions may be convex or concave.

Surface Feature Configurations

Any of the waveguides disclosed herein may have light extraction features which have geometries and/or dimensions similar to or the same as the following exemplary embodiments.

A. Prismatic Structures. There are unlimited combinations of thickness, riser angles, and extraction angles for prismatic structures, and one size does not necessarily fit all. The correct extraction surface size may depend on a number of factors including the thickness of the waveguide, the extraction and riser surface angles, as well as allowable light losses due to scattering.

Figure 18:
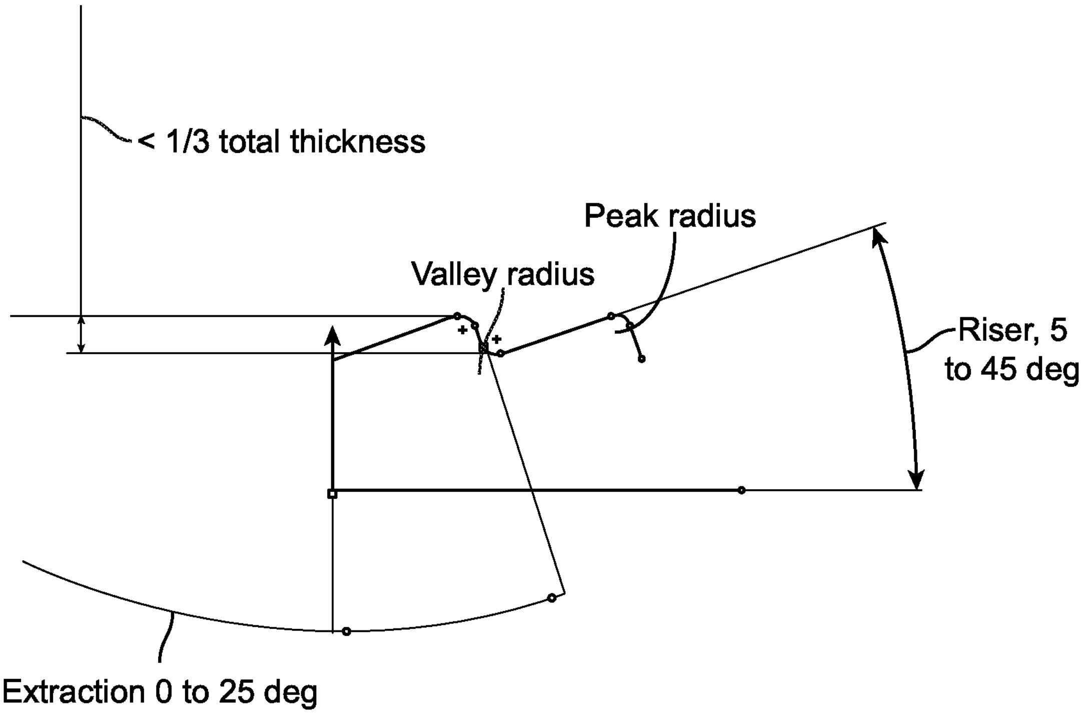
FIGS. 18-22 illustrate various features of prismatic light extraction structures.
Figure 19:
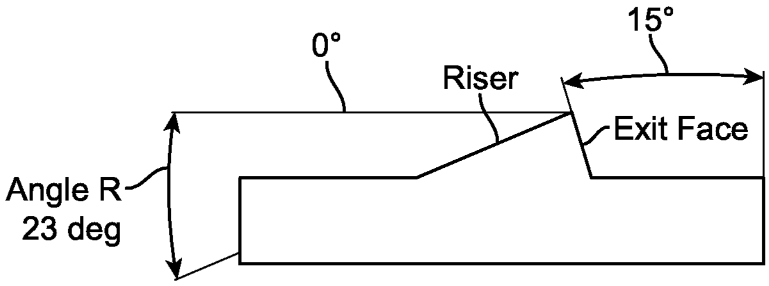

Groove depth (here the distance between the top of the riser and the bottom of the exit face) is preferably no more than ⅓ to ⅕ of the part thickness. If the grooves are too deep, more than ⅓ the total thickness of the part, then plastic flow may be restricted and it may be difficult to injection mold the part due to high internal stresses, warping and the part may be excessively brittle. For example, for a 1 mm thick part, groove depth is preferably no deeper than 0.33 mm. For a 2.5 mm waveguide, groove depth is preferably no deeper than 0.83 mm. FIGS. 18-19 illustrate the riser and exit face which form stair steps in a prismatic light extraction structure. Each step has a riser and exit face. Various references lines or planes may be used to measure riser and exit face angles. For example, a plane parallel to the rear surface of the part may be used to measure the riser angle, and another plane perpendicular to the top surface of the part may be used to measure the exit face angle.

The groove depth may be any depth, but is preferably ⅓ to ⅕ the part thickness for at least the following reasons. Each groove has a peak and a valley, each with a radius. The radius of the peak and the radius of the valley are determined based on the tools used to fabricate the part or the tools used to cut the part or mold, and/or based on the filling characteristics of the radius during molding of the part. Thus at the base and the peak of the grooves, the surfaces are rounded. During fabrication of the part such as during injection molding, the polymer may have difficulty flowing into and completely filling the grooves if the radii are too small. A radius of curvature of about 5 or 6 microns or greater is reasonable for both the peak and valley radii. Because the peak and valley radii remain fixed regardless of the dimensions of the extraction features, for a very small groove, the peak and valley radii take up a larger portion of the groove and thus the groove may not fill properly. For example, assuming a 5 or 6 micron radii on the peaks and valleys and a 20 micron groove, 10 to 12 microns are consumed by the radii. However, for a larger groove, the percentage of the groove consumed by the radii will be negligible and therefore more of the groove will fill properly. For example, if the groove is 1 mm, then considerably less of the groove is consumed by the radii.

To determine minimum groove width, an acceptable percentage for scattering is selected and then the minimum acceptable groove width is calculated. Groove depth should be deep enough such that in preferred embodiments no more than 5% to 10% of the surface area is consumed by groove peak and valley radii. Less is actually preferred. In the example below, 5% acceptable scatter was used and a preferred groove width was estimated to be 0.064 mm as the groove width. Acceptable scatter preferably ranges from about 1% to about 5%, and may be quantified as the ratio of total riser radius and valley radius to the total groove width. The calculations below are based on 5% scatter, but may be repeated using any value of scatter and preferably any value between 1% and 5%.

The following example illustrates various calculations related to the dimensions of the prismatic structures. Consider a simple groove with a fixed riser angle of 15 degrees and an extraction angle of 90 degrees (vertical). Assume the groove has a valley radius at it base, a length of correctly formed groove, and at the tip, a peak radius, and the following:

A=Riser angle

Rv=Valley Radius=0.006 mm

Rp=Peak Radius=0.006 mm

W=Total groove width

H=groove height

L=allowable loss=5%

T=Waveguide thickness=1 mm

Equations (1), (2) and (3) allow calculation of the minimum recommended length and height of each groove.

$$\frac{R_v + R_p}{w} = L\frac{0.012}{w} = 0.05\ W = 0.24\text{ mm}\ \frac{H}{w} = \tan(A) \quad (1)$$

$$H_{min} = W\tan(A)\ H_{min} = 0.24\tan(15°)\ H_{min} = 0.064\text{ mm} \quad (2)$$

$$H_{max} = T/3\ H_{max} = 0.33\text{ mm} \quad (3)$$

Therefore, in this example the groove depth should be less than 0.33 mm and greater than 0.064 mm. But, one of skill in the art will appreciate that these dimensions are not intended to be limiting and that they may change. They can change depending on the total thickness of the part, the quality of the tooling and molding, the acceptable losses to scattering, and the design of the riser and extraction faces.

The extraction features have a riser and an exit surface, as seen in FIG. 19. The riser is designed to determine the frequency of features which will appear along the length of the waveguide. For the current preferred design, the height of each of the features is the same, so if the riser angle is small, it will cause the length of the feature to be long. That is since the length of the features is longer, less features per inch result along the length of the waveguide (lower pitch). Since there are fewer features along the length, more light will be pushed down, and most of the light will come out of the distal end vs. the face of the waveguide. If the riser angle is large (greater pitch), there will be more features, and more light will come out with more proximal features and less will recycle distally down towards features below. So, the waveguide will appear to have more light coming out of the front surface versus the distal tip. Preferred embodiments have a design with light extraction structures such that the structures generate an evenly balanced output along the length of the device. This is preferred because when any portion of the waveguide is blocked, the other portions will provide sufficient lighting to the target to compensate for whatever losses are created by the blockage.

The riser may be measured relative to the rear surface of the waveguide or relative to a plane that is parallel to the rear surface. In preferred embodiments, the riser angle will range between −16 degrees and 72 degrees (based on the numerical aperture NA of 0.55 NA input light source and index of refraction of the waveguide material of 1.53). More preferred embodiments have further optimized riser angle values of between 18 degrees and 24 degrees. At below 12 degrees, most light will be pushed towards the distal end and not much light is extracted along the length of the waveguide. At 72 degrees is the critical angle and all the light will be extracted out of the riser surface. Preferred embodiments have light extracted only out of the exit surface, not the riser surface.

Figure 20:
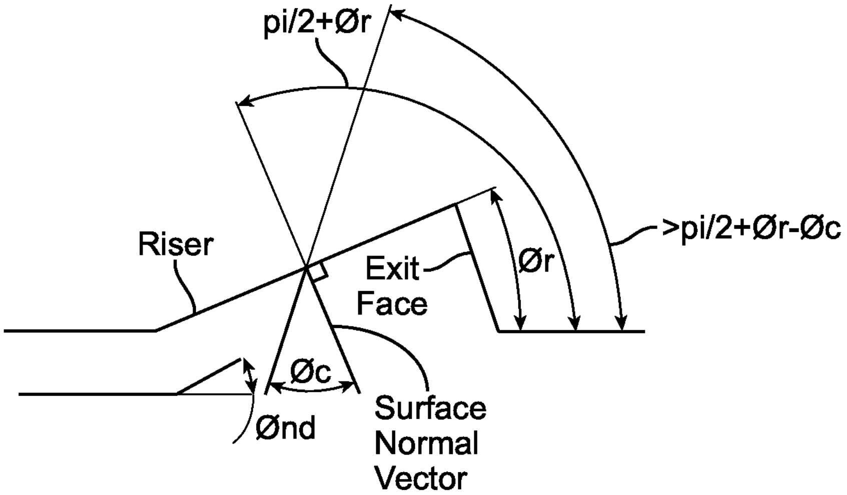

These angles are based on the axis described in FIG. 19 and also FIG. 20. The critical angle for the riser is defined as:

$$\theta = \text{Location of critical angle for the riser (with angle } \varphi_r) = \frac{\pi}{2} + \varphi_r - \operatorname{asin}(n_1/n_2)$$

$\varphi_r$=Riser Angle $\varphi_c$=Critical Angle=asin $(n_1/n_2)$ $\varphi_{na}$=extreme half angle of source=asin (NA)

$n_1$=Index of refraction of air=1.00029

$n_2$=Index of refraction of the material of the optical device, typically 1.33 to 2.0

$\theta > \varphi_{na}$

The exit surface from FIG. 19 is designed to direct or point the light towards the target. For preferred embodiments of the waveguides disclosed in this application, exit face angles preferably range between 1° and 65° (based on the numerical aperture NA of 0.55 NA input light source and index of refraction of the waveguide material of 1.53). A more preferred embodiment currently uses a 15° exit face angle. These angles are from the vertical axis perpendicular to the top or front surface of the waveguide as seen in FIG. 20. If the angle approaches the critical angle, no light will come out of the feature and will be pushed down towards the bottom or distal end.

Figure 21:
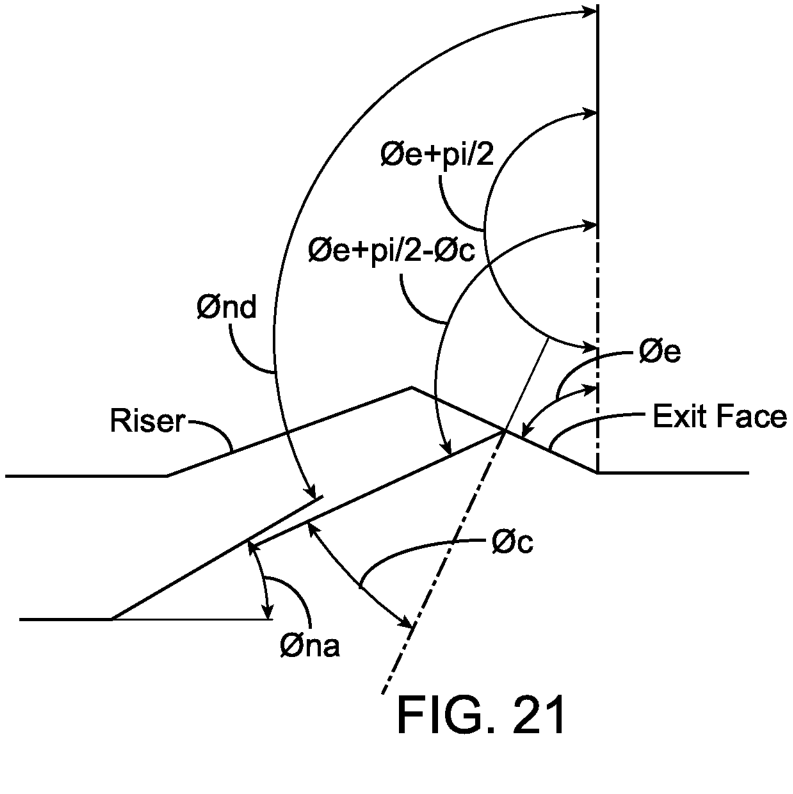

The relationships for the exit face are shown in FIG. 21. A relatively flat angle is shown in FIG. 21 in order to demonstrate the concept. The same angle relationships hold as in the riser angle. However, the angles are now referenced to the vertical.

$$\theta = \text{Location of critical angle for the exit face angle (with angle } \varphi_e) = \frac{\pi}{2} + \varphi_e - \operatorname{asin}(n_1/n_2)\ \theta > \varphi_{na}$$

$\varphi_e$=Exit Face Angle $\varphi_c$=Critical Angle=asin $(n_1/n_2)$ $\varphi_{na}$=extreme half angle of source=asin (NA)

$n_1$=Index of refraction of air=1.00029

$n_2$=Index of refraction of the material of the optical device, typically 1.33 to 2.0

$\theta > \varphi_{na}$

Therefore, preferred values (but not intended to be limiting) for extraction features may be:

For a 1 mm×7 mm×20 mm waveguide, groove depth=0.064 mm to 0.33 mm. For a 2.5 mm×8 mm×30 mm waveguide, groove depth=0.064 mm to 0.83 mm. Riser angle ranges from 5° to 45° and more preferably from 0 to 25 degrees. Extraction angle ranges from 0° to 25°. A flat riser and deep groove depth will create the largest groove width, or pitch. Groove width will be between 9.48 mm for an extreme case of a 2.5 mm thick waveguide with 0.83 mm groove depth and 5° riser. A steep riser and shallow groove depth will create the smallest groove width, or pitch. Groove width will be the other extreme, 0.064 mm for 45° riser, and 0.064 mm groove depth. Preferably, groove depth is constant along a waveguide but the groove width may vary. Other embodiments where groove depth is variable are also contemplated. Grooves may be aspheric such that the light is modified by the extraction structures gradually, in an analog manner. Waveguides also preferably have an angled distal tip that captures remaining light that has not been extracted by the surface features. Other preferred angles (but not intended to be limiting) for waveguides are summarized in the table below. Values are based on index of 1.53, NA 0.55.

| Design Type | Riser Angle | Exit Face Angle |
|---|---|---|
| Current Preferred Embodiments | 18.9-23° variable | 15° |
| No Input Stem | 12° | 1° |
| Straight Input Stem | 16° | 4° |
| Input Stem with Tight Curve | 16° | 16° |
| Other Embodiments | 11° | −20° (340°) |

Figure 22:
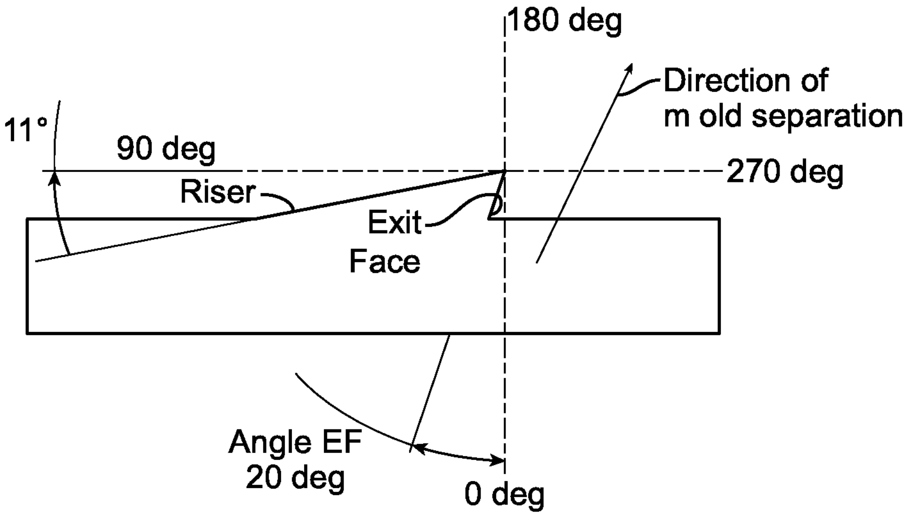

Waveguides may have extraction features with negative exit face angles as seen in FIG. 22. However, these are not generally used when the negative exit face angles are optimized for a waveguide having no input stem, where the light source butts up directly to the features. Additionally, having negative exit face angles creates an undercut region which is difficult to process due to complex molding process where the mold has to separate parallel to the exit surface thus putting a parting line directly visible on the part. A visible parting line which is parallel to the device will create glare when light hits it. Preferred embodiments of the present waveguide have a parting line which does not interact with light propagation.

Therefore, in summary, the prismatic light extraction features may include:

Height of extraction features (or groove depth)—the features preferably have constant heights and varying widths. The heights may be designed based on manufacturing capabilities and preferably range between 64 microns and ⅓ of the thickness of the part.

The distal end of the waveguide may provide further light shaping. It can be flat or angled with lenslets on the surface to better mix the light. Exemplary distal waveguide ends are disclosed in U.S. Pat. No. 8,088,066; the entire contents of which are incorporated herein by reference.

Dead zones are areas along the stem or the extraction portion where the light does not interact with the surface and thus there is no or substantially no total internal reflection. These dead zones are ideal places to glue mechanical features in order to attach the waveguide to retractor blades for example. Since no light exists in the dead zones, light will not leak from these locations when something is glued to the waveguide. Dead zones are also disclosed in further details in U.S. Pat. No. 8,088,066; the entire contents of which are incorporated herein by reference.

Figure 23:
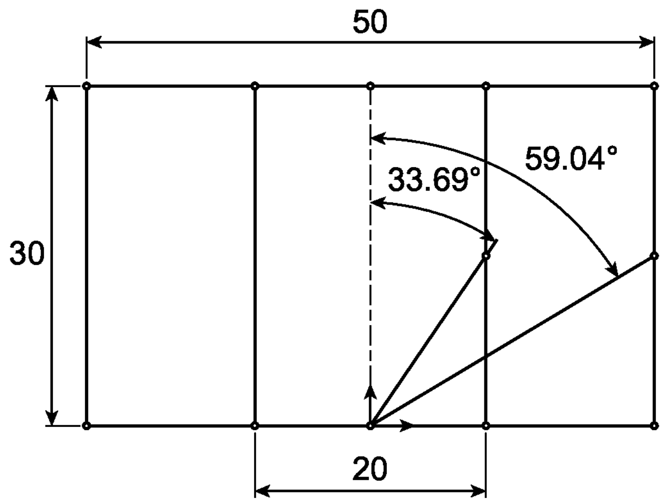
FIGS. 23-24 illustrate various features of lenticular light extraction structures.

B. Lenticular Array or Structures. The purpose of the lenticular array is to spread the light output pattern and control lateral divergence (also referred to as the horizontal direction relative to the longitudinal axis of the waveguide) without changing waveguide thickness. FIG. 23 is a comparison of primary angles for a 20 mm (W)×30 mm (L) pattern and a 50 mm×30 mm pattern. The inner and outer rectangles represent the two patterns. Using a flat back side with no lenticular array results in an output pattern that is approximately 20 mm wide×30 mm long. The diagonal lines represent a vector from the waveguide to the center of the right edge of the pattern. These simple angles demonstrate that to make a 20 mm wide pattern into a 50 mm wide pattern, the viewing angle of the waveguide must be expanded by at least 26°.

The geometry below explains the function of the lenticular. Each lenticular is a portion of a cylinder. Assume that light strikes the lenticulars from directly forward even though light rays will strike the lenticulars from various angles within the numerical aperture NA of the source and the acceptance NA of the waveguide, whichever is less. However, an average ray would be one originating from directly forward. For a quick calculation it is easier to work with this one ray.

Figure 24:
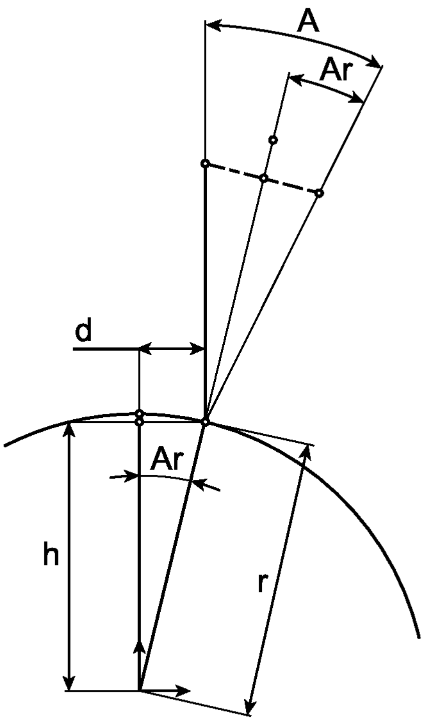

Equations (4) and (5) below are used to calculate various aspects of the lenticulars including pitch and the radius of curvature. FIG. 24 illustrates the various dimensions referenced in equations (4) and (5), where:

A=Deflection angle=26.3 degrees

Ar=Ai=Reflection and Incidence angles=A/2 d=lenticular half width r=lenticular radius h=height of lenticular edge (used later)

$$\frac{d}{r} = \sin(A_r) \quad r = \frac{d}{\sin(A_r)}$$

A lenticular array with millions of lenticulars creates the best mixing of light. However, the realities of manufacturing are that there will be a small defect area between each lenticular. This defect area is primarily caused by the radius of the tool used to cut the part and this radius is fixed. Therefore, as in the prisms previously discuss or other light extraction features, the lenticular size is tied to the amount of scattering that is acceptable. A very low amount of scattering is assumed in this example. In the case of the extraction features, scattered light will probably fall somewhere on the target plane and may still be useful. In this case, some scattered light will probably exit out the back or rear surface of the waveguide.

Rv=valley radius=0.006 mm

L=allowable loss due to scattering=1% d=lenticular half width from above $$\frac{R_v}{2L} = d$$

$$\frac{R_v}{2L} = d \tag{4}$$

$$d = 0.3 \text{ mm}$$

This permits calculation of r. The minimum pitch of the lenticular is 0.6 mm. The radius of the lenticulars is dependent on the pitch. For this pitch, the radius of curvature is 0.68 mm. To calculate the maximum pitch and radius waveguide desired thickness is maintained at the peak of the lenticular. Therefore the lenticular edges will penetrate into the device. In preferred embodiments this does not extend into the part more than about ⅓ of the total thickness of the waveguide, for manufacturing reasons.

From the geometry of part:

$$r - h = t/3 \quad h = r\cos(A_r), \text{ solving for both,}$$

$$r = \frac{t}{3(1-\cos(A_r))}$$

$$r = \frac{d}{\sin(A_r)} \tag{5}$$

If t=1 mm and A=26.3 degrees, then r=3.22 and d=7.26 mm. This is the maximum groove pitch. This number is quite large, so preferred embodiments work within the constraints of the minimum dimensions.

Typical values for the lenticulars may include:

Minimum recommended pitch=0.3 mm.

Radius of curvature=0.68 mm.

Maximum pitch=18.1 mm, this is larger than the waveguide width, so it is substantially a single curved surface.

Maximum radius of curvature=8.05 mm.

Other embodiments disclosed herein include a cross lenticular array or pillowed array. The same analysis used above applies to these embodiments as well, but it must be performed in both the vertical as well as horizontal directions. Additionally, lengthening of the pattern has proven to be more efficiently accomplished by modifying the angles of the extraction features. Waveguides in this disclosure also are preferably between 0.5 mm and 1 mm thick. While still possible, thinner than 0.5 mm becomes difficult to mold and hard to keep flat.

Shapeable Waveguide

Figure 7:
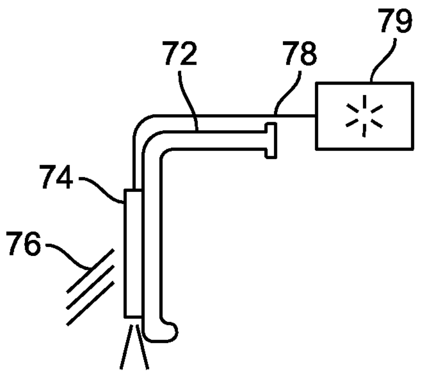
FIG. 7 illustrates a waveguide coupled to a surgical retractor.
Figure 8A:
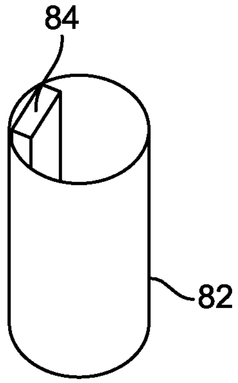
FIGS. 8A-8B illustrate a waveguide coupled to a tubular surgical retractor.
Figure 8B:
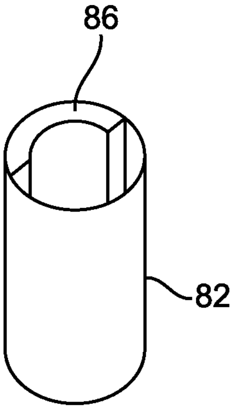

FIG. 7 illustrates an optical waveguide 74 coupled to a surgical retractor blade 72. A fiber optic cable 78 delivers light from an external source 79 to the waveguide 74. Light 76 extracted from the waveguide illuminates a surgical field or other work space. FIG. 8A illustrates a cannula retractor 82 for retracting tissue and creating a circular surgical field. An optical waveguide 84 is coupled to the waveguide 82 and disposed in the central bore of the cannula for illuminating the surgical field. FIG. 8B illustrates a similar example where a curved waveguide 86 is coupled to the cannula retractor 82. In the examples of FIGS. 7 and 8A-8B, the waveguide either does not conform smoothly to the surface of the retractor or it may take up excessive space thereby limiting an already small surgical field. Therefore, it would be desirable to provide waveguides for illuminating a working area such as a surgical field that conform more evenly with the working area and/or any tools or instruments, as well as having lower profiles that do not occupy an excessive amount of space.

Figure 9A:
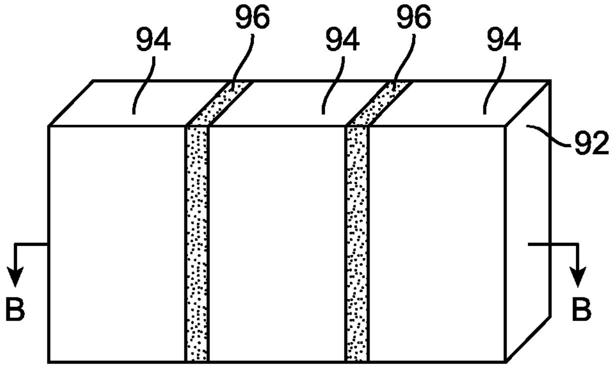
FIGS. 9A-9D illustrate an exemplary embodiment of a shapeable waveguide.
Figure 9B:
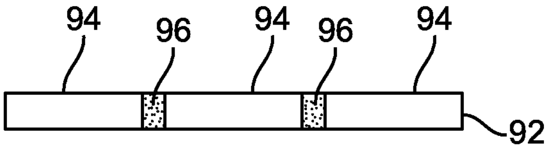
Figure 9C:
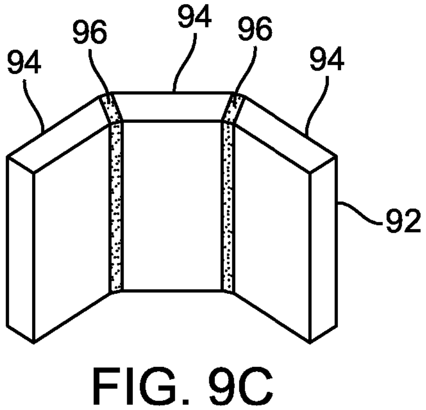
Figure 9D:
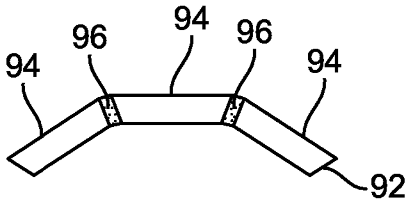

FIGS. 9A-9D illustrate an exemplary embodiment of a flexible and shapeable waveguide. The waveguide 92 includes two or more thin optical waveguides 94 that are coupled together with a flexible material 96 that acts as a hinge. FIG. 9B shows a cross section taken along the line B-B in FIG. 9A. The waveguides may be flexed to form various shapes such as a curved shaped as seen in FIG. 9C and FIG. 9D illustrates a top view of FIG. 9C. Therefore, by having many narrow waveguides, the assembly may be shaped into smooth curves that can form any shape, include a semi-circle or various polygons. The shape may be adjusted to match a tool or other surgical instrument and the two may be coupled together.

Figure 10A:
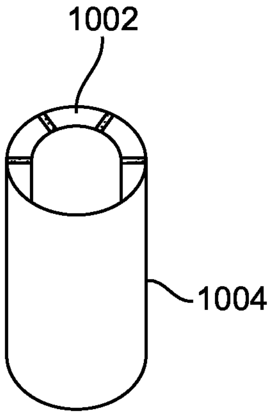
FIGS. 10A-10B illustrate a shapeable waveguide conforming to and attached to a retractor.
Figure 10B:
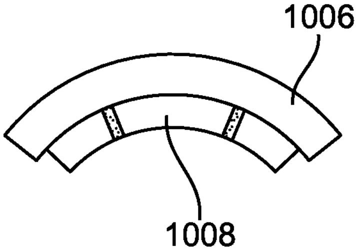

FIG. 10A illustrates a shapeable waveguide such as the embodiment illustrated in FIGS. 9A-9D shaped to conform to the inner circular surface of a cannula retractor 1004. FIG. 10B similarly shows a shapeable waveguide such as the embodiment in FIGS. 9A-9D shaped to conform to the curved surface of a curved retractor blade 1006. While these embodiments show the shapeable waveguide having three segments of waveguide coupled together with two flexible sections, one of skill in the art will appreciate that this is not intended to be limiting and that any number such as 4, 5, 6, 7, 8, 9, 10, or more segments of waveguide may be assembled together and held together with the flexible material to form the shapeable waveguide.

Figure 11A:
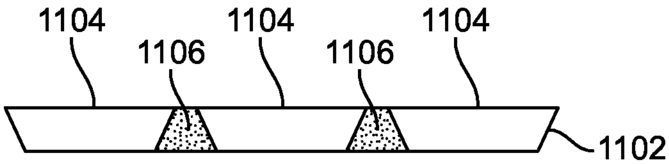
FIGS. 11A-11B illustrate an exemplary embodiment of a shapeable waveguide made up of trapezoidal waveguide segments.
Figure 11B:
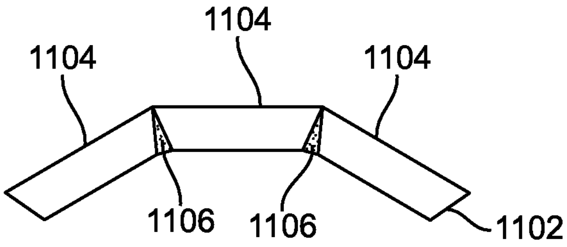
Figure 11C:
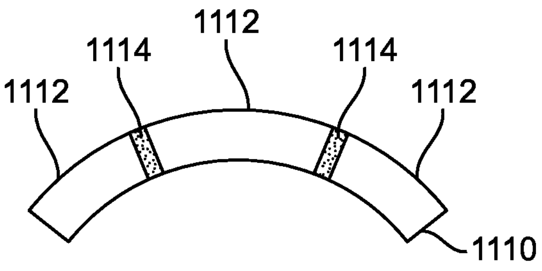
FIG. 11C illustrates an exemplary embodiment of a shapeable waveguide made up of curved waveguide segments.

The waveguides disclosed above have rectangular cross-sections. However this is not intended to be limiting. In other embodiments the cross-section may be trapezoidal such as seen in FIGS. 11A-11B. The trapezoidal configuration creates a natural expansion and contraction joint between the waveguides. FIG. 11A shows a shapeable waveguide 1102 having three trapezoidal waveguides 1104 coupled together with a flexible material 1106 such as silicone. The shapeable waveguide 1102 maybe shaped from a linear configuration to a curved configuration like FIG. 11B in order to conform to the work area or any adjacent tools. The trapezoidal configuration allows the waveguides to freely pivot relative to one another without binding. The waveguides may also have curved cross-sections such as in FIG. 11C where the shapeable waveguide 1110 includes three or more curved waveguide segments 1112 separated by flexible material 1114 that form hinges so that a smoother curve may be formed than in the embodiment of FIG. 11A-11B.

Figure 11D:
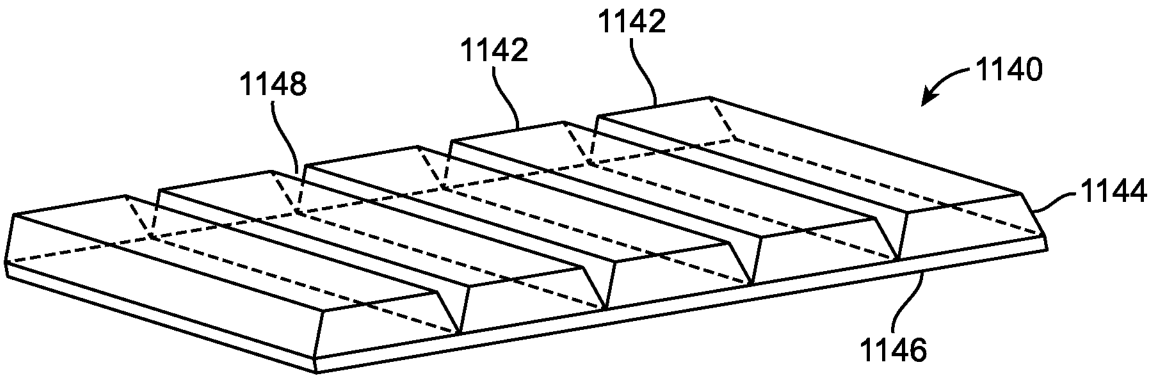
FIGS. 11D-11E illustrate an alternative embodiment of a shapeable waveguide.
Figure 11E:
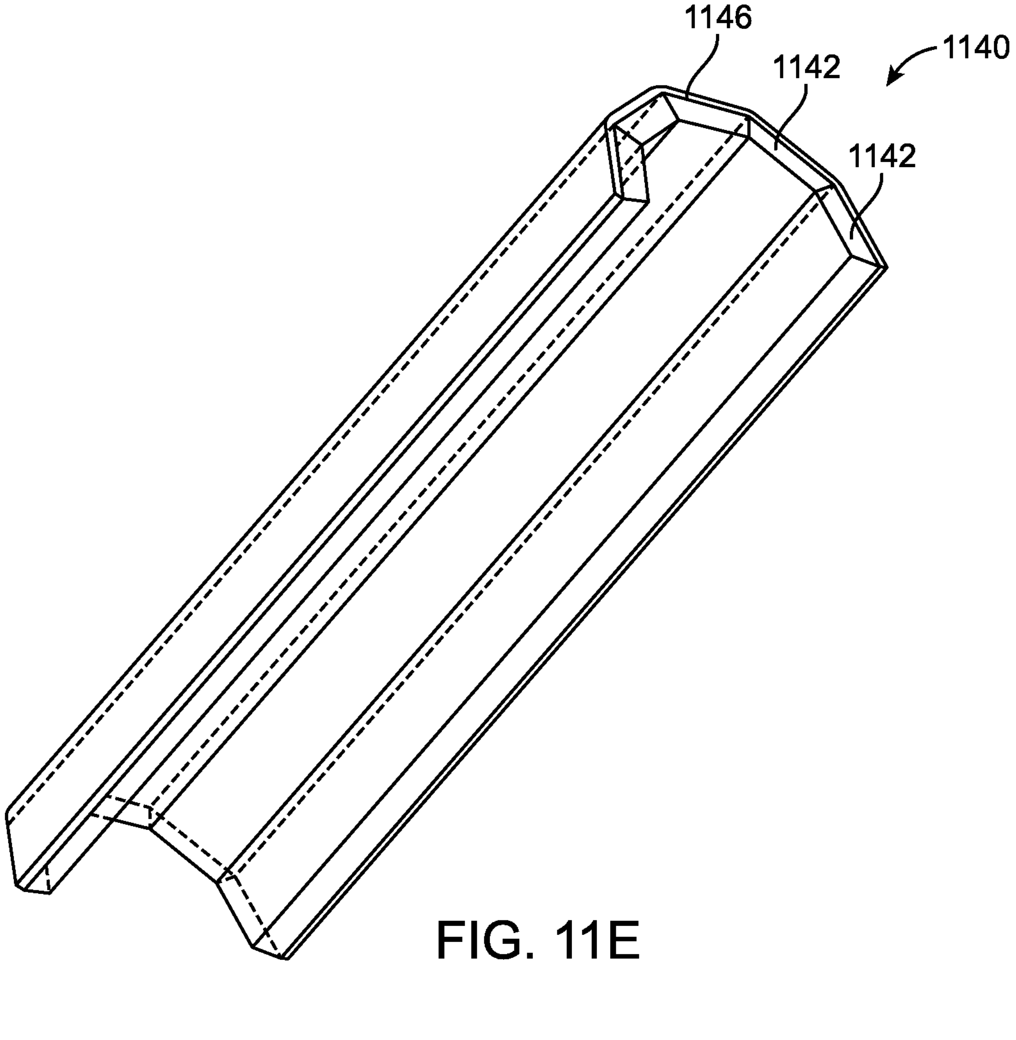

FIGS. 11D and 11E illustrate an alternative embodiment of a shapeable waveguide. This embodiment is similar to that in FIGS. 11A-11B, with the major difference being that the waveguide segments are secured to a flexible backing instead of having a flexible material between adjacent segments. FIG. 11D illustrates an assembly 1140 of segmented waveguides 1142 each having a trapezoidal cross-section 1144. The segmented waveguides are attached to a flexible substrate layer 1146 such as silicone or any other resilient material. The trapezoidal cross-section creates a gap 1148 between adjacent segments 1142 that allows the assembly to be bent into other configurations without the segment edged binding. The gap is preferably triangular shaped and runs parallel to the segments the entire length of the segments. FIG. 11E illustrates an exemplary embodiment where the assembly 1140 of segmented waveguides has been manipulated into a curved semi-cylindrical shaped waveguide. The individual waveguide segments or the assembly may utilize any of the features disclosed herein, including but not limited to the use of surface features to extract and control light, as well as the light input features.

Figure 12A:
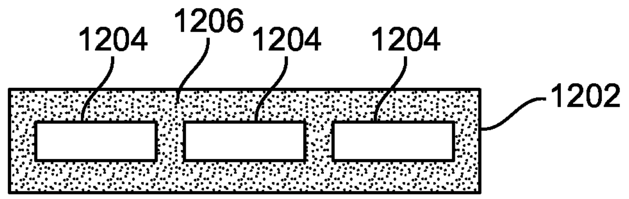
FIGS. 12A-12B illustrate exemplary embodiments of shapeable waveguides.
Figure 12B:
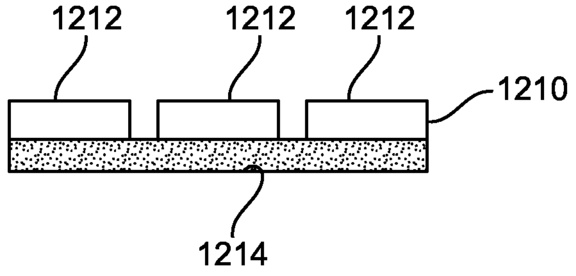

The waveguides may have a thin elongate bead of flexible material coupling them together along the longitudinal seam separating adjacent waveguides as seen in FIG. 9A, or the shapeable waveguide 1202 may have multiple waveguides 1204 that are encapsulated in a flexible layer of material 1206 as seen in FIG. 12A. In an alternative embodiment the shapeable waveguide 1210 may have a plurality of waveguides 1212 attached to a substrate 1214 such as a flexible film or adhesive tape as seen in FIG. 12B.

Figure 13:
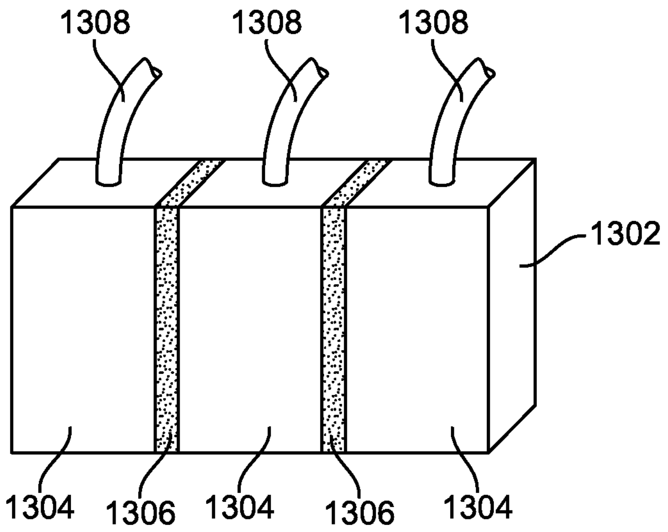
FIG. 13 illustrates light inputs for a shapeable waveguide.

Light may be delivered to the shapeable waveguide in any number of ways. For example, in FIG. 13 the shapeable waveguide 1302 includes a plurality of waveguides 1304 coupled together with a flexible material 1306 that can act as a hinge. Each waveguide 1304 is coupled with a fiber optic 1308 that can be optically coupled with one or more external light sources. The fiber optic may 1308 may be bonded to a receiving channel in the waveguide, or the waveguide may be overmolded onto the fiber optic. In still other embodiments, the fiber optic cables 1308 are replaced by integrally formed input stems that transmit light from the light source to the waveguide. In still other embodiments, a single light input fiber optic cable or input stem is used to bring light to the shapeable waveguide. An optical manifold is then used to distribute and deliver light to each waveguide segment in the assembly.

Figure 14A:
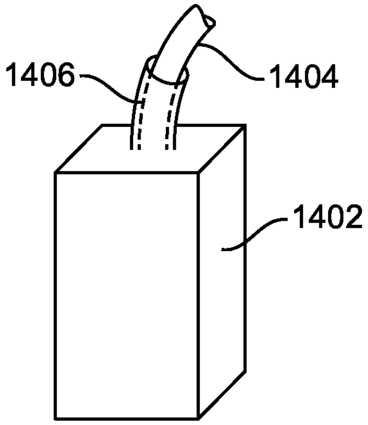
FIGS. 14A-14B illustrate embodiments of strain reliefs.
Figure 14B:
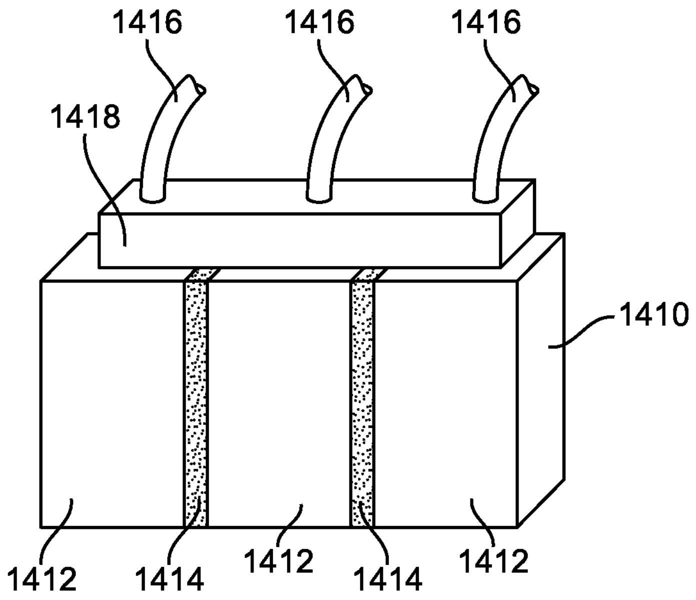

Because the shapeable waveguides are actuated and manipulated, it is often desirable to provide a strain relief on the input stem or fiber optic input cable to prevent damage. FIG. 14A illustrates one waveguide segment 1402 of a shapeable waveguide with an input fiber optic 1404 and a strain relief 1406 to prevent damage to the fiber optic. The strain relief may be a resilient polymer such as silicone. Each individual fiber optic input cable may have its own strain relief, or a manifold strain relief may be used as seen in FIG. 14B where the shapeable waveguide 1410 includes several waveguide segments 1412 coupled together with a flexible material 1414. A manifold 1418 of resilient material acts as a strain relief for each of the light input fiber optic cables 1416.

Figure 15:
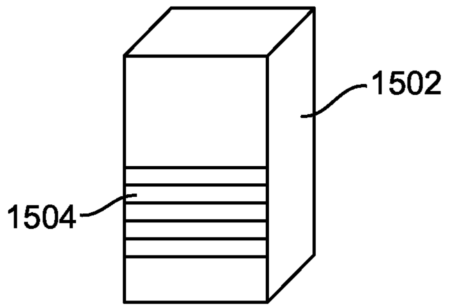
FIG. 15 illustrates the use of light extraction surface features on a shapeable waveguide.
Figure 16:
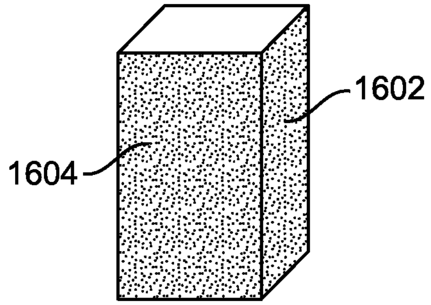
FIG. 16 illustrates the use of a coating, cladding or film on a shapeable waveguide.

Any of the waveguide segments in the shapeable waveguides described herein may also have surface features to extract and control the direction of the extracted light. FIG. 15 illustrates a waveguide segment 1502 having prismatic features 1504 like those described previously. The surface features may be on a front, rear or any surface of the waveguide segments. Any of the surface features described herein may be used to extract and control light from a shapeable waveguide. Additionally, FIG. 16 illustrates the use of a coating, cladding or film 1604 disposed over a waveguide segment 1602 of a shapeable waveguide. The coating, cladding or film may have an index of refraction that helps promote total internal reflection of light within the waveguide segment. The index of refraction of the coating or cladding is preferably lower than the index of refraction of the waveguide. An exemplary range of the index of refraction is between about 1 and 1.5. In still other embodiments, the film may have surface features which help extract and control light. Additionally, in addition to, or instead of coatings or claddings, an air gap may be disposed between the waveguide and any adjacent structure to help prevent light loss.

Figure 17:
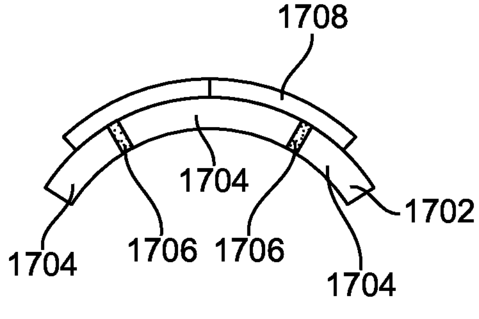
FIG. 17 illustrates the use of a stabilizing member to hold the shapeable waveguide in a desired configuration.

Once the shapeable waveguide has been manipulated into a desired configuration it may be coupled with a stabilizing member 1708 to hold its position as seen in FIG. 17. Here the shapeable waveguide 1702 includes a plurality of waveguide segments 1704 coupled together with a flexible material 1706. It has been formed into a curved assembly and stabilizing member 1708 locks the assembly into position. The stabilizing member may use adhesives, fixtures such as screws, snap fits, or other mechanisms known in the art to attach to the shapeable waveguide.

Figure 25A:
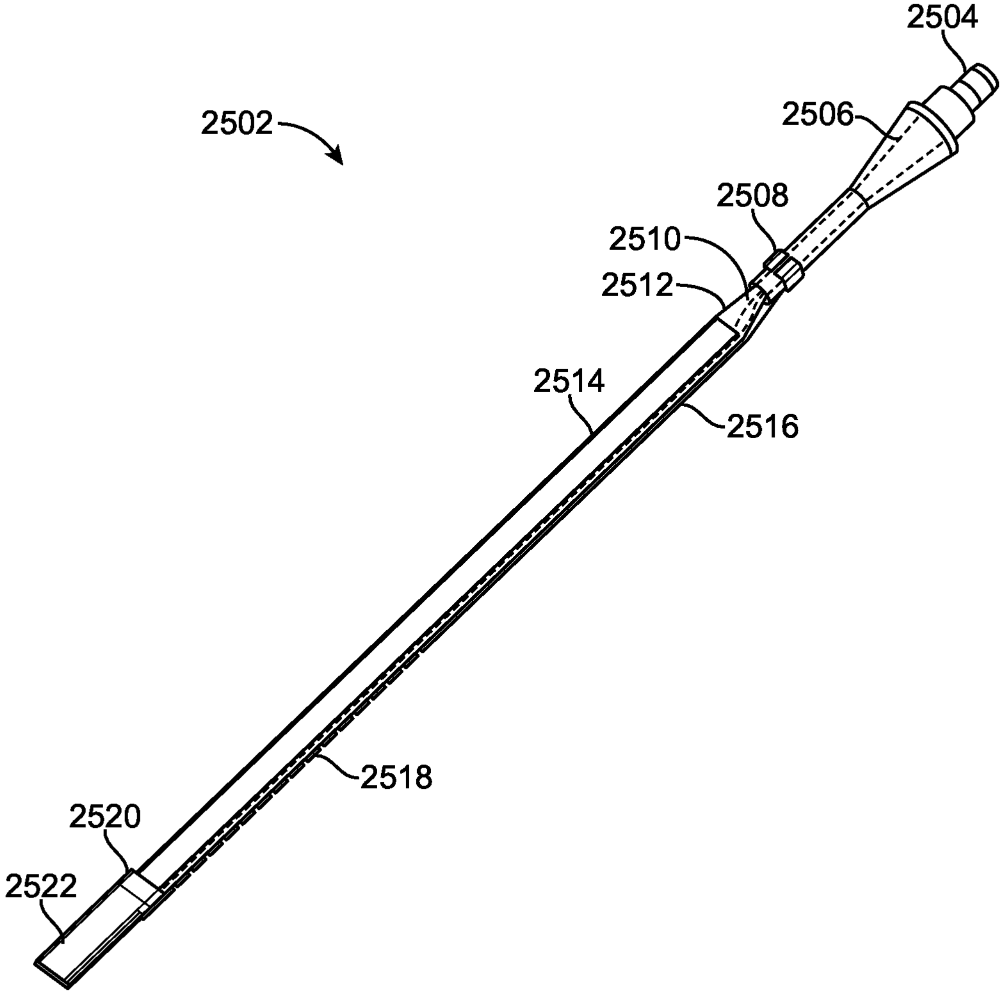
FIGS. 25A-25I illustrate another shapeable optical waveguide.
Figure 25B:
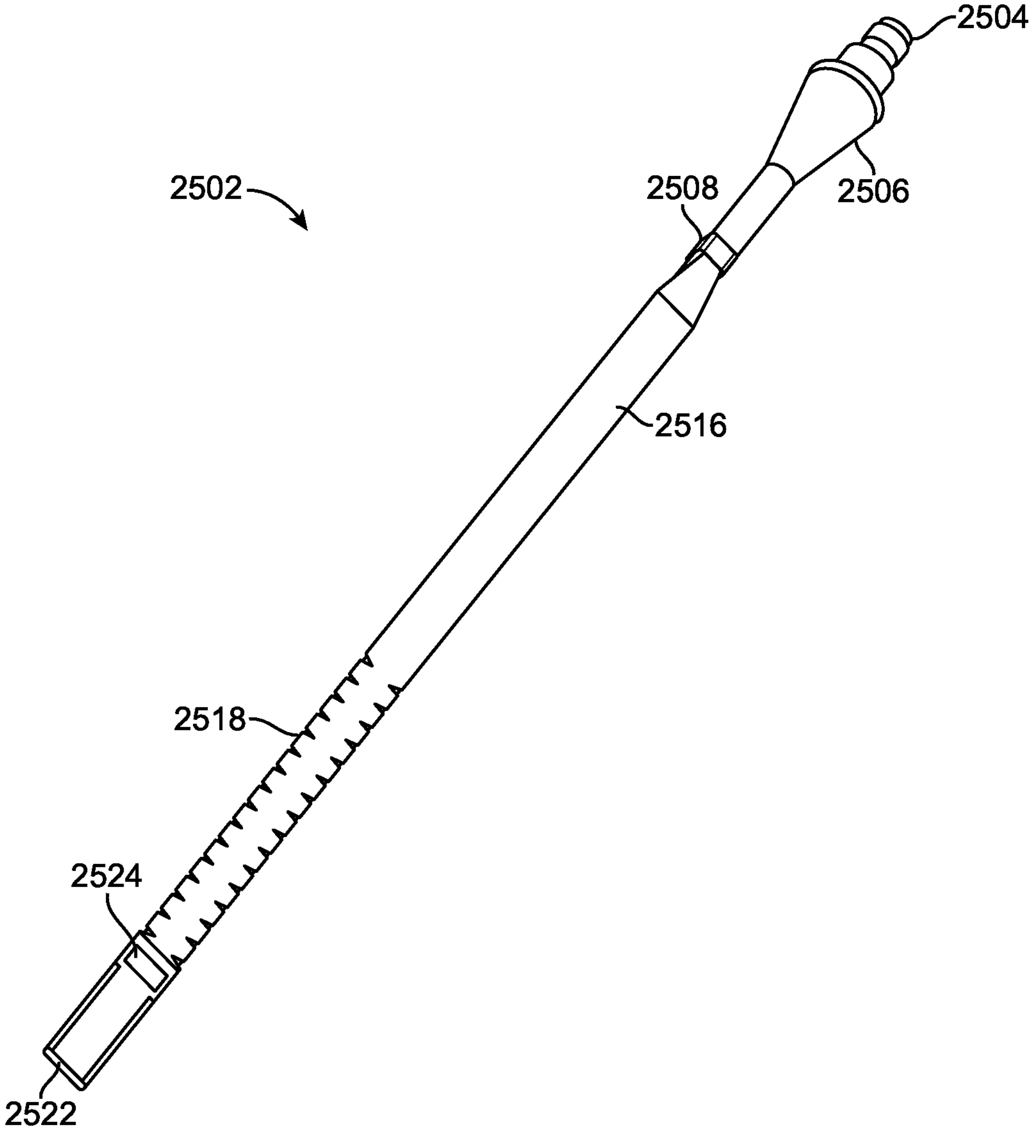

FIGS. 25A-25I illustrate another embodiment of a shapeable optical waveguide 2502. This instrument may be shaped to conform to a work field such as a surgical field or it may be shaped to conform to a tool such as a surgical instrument like a retractor. FIG. 25A is a top perspective view of the shapeable waveguide assembly 2502. The waveguide assembly 2502 includes a connector 2504, strain relief 2506, crimping band 2508, fiber optic bundle 2510, malleable backing element 2516, hinge 2518, sleeve 2520 and a non-fiber optic optical waveguide 2522. The proximal end of the shapeable optical waveguide assembly 2502 includes a connector such as an ACMI standard optical connector 2504 that can be used to couple the shapeable optical waveguide assembly 2502 with a light source. Other connectors may also be used such as a barbed fitting or others known in the art. A fiber optic bundle 2510 is coupled to the connector 2504 and allows light to be transmitted from the light source (not shown) through the optical connector 2504 to the non-fiber optic optical waveguide assembly 2522. A strain relief 2506 may be disposed over the fiber optic bundle 2510 to prevent unwanted kinking or other damage to the fiber optic bundle. The fiber optic bundle is preferably configured in a cylindrically shaped bundle at the proximal end of the shapeable waveguide with a flaring portion 2512 where the bundle flares out into its final flat planar configuration 2514 and eventually is coupled with the non-fiber optic optical waveguide 2522. A sleeve 2520 is used to join the fiber optic bundle to the optical waveguide 2522. The non-fiber optic optical waveguide 2522 is coupled to the malleable backing element 2516 along with the fiber optic bundle 2514. A crimping band 2508 helps couple the fiber optic bundle 2514 to the malleable backing element 2516. A hinge 2518 on the malleable backing element facilitates bending and manipulation of the backing element into a preferred shape during use. FIG. 25B illustrates a bottom perspective view of the shapeable waveguide assembly 2502. An engagement window 2424 is visible in this view. The window 2524 is disposed in the malleable backing 2516 near its distal end and allows the optical waveguide 2522 to engage with the backing 2516. The hinge 2518 may be a series of triangular cutouts from the backing 2516 axially along the backing on both edges. The hinge 2518 allows the backing to be manipulated by an operator and bent into any desired configuration.

Figure 25C:
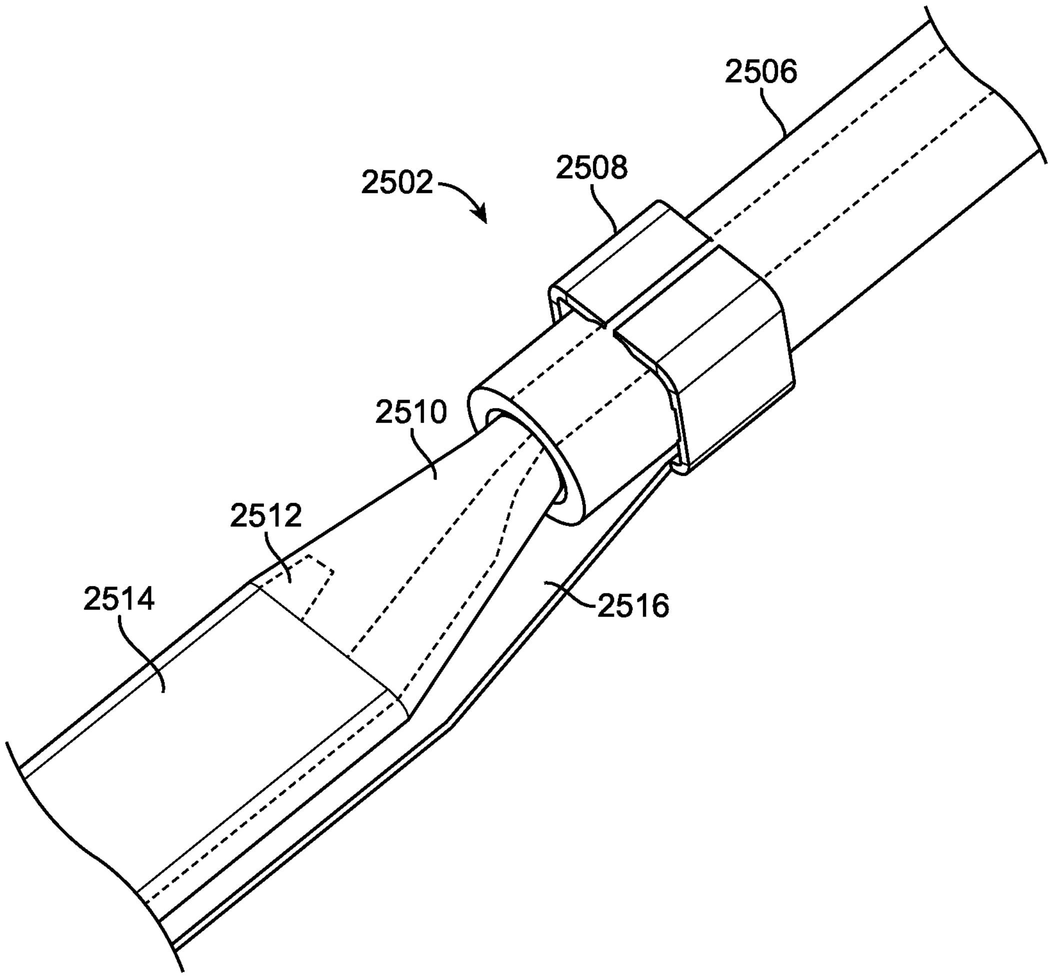

FIG. 25C highlights features of a proximal portion of the shapeable waveguide assembly 2502. The fiber optic bundle 2510 is initially cylindrical and then it flares outward 2512 into a flat, rectangular and planar bundle of fibers 2514. The planar bundle of fibers 2514 not only helps reduce overall profile of the fibers to minimize the space the device occupies, but also helps transmit light into and fill the optical waveguide 2522. An outer strain relief 2506 helps prevent kinking of the fiber optic bundle and crimping band 2508 couples the fiber optic bundle and strain relief onto the malleable backing element 2516.

Figure 25D:
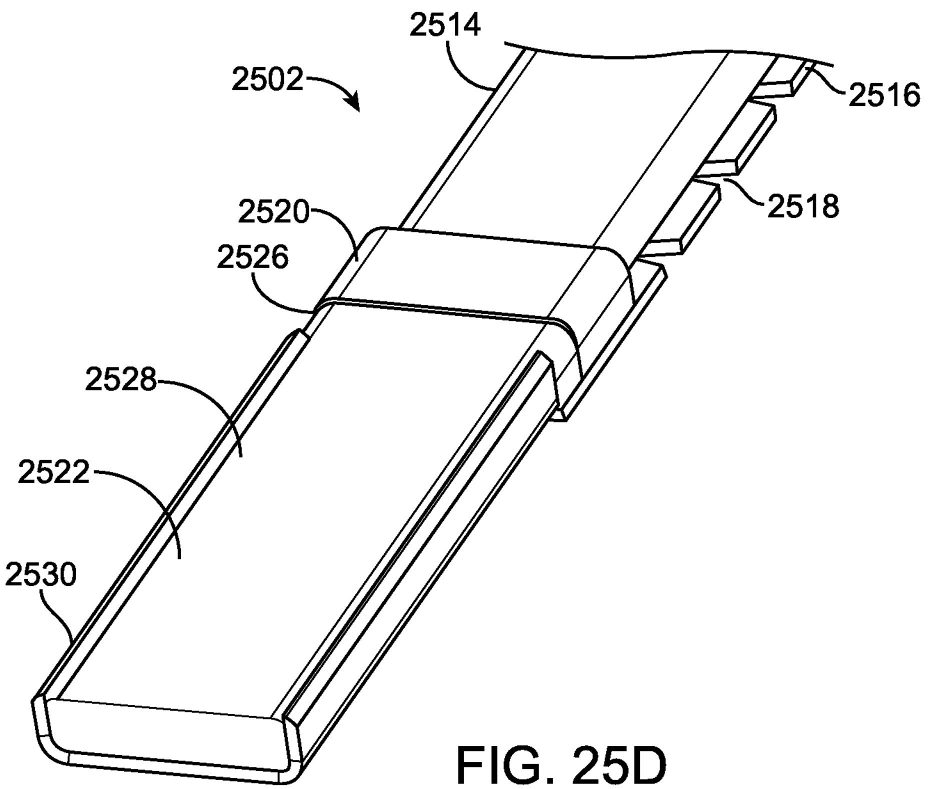

FIG. 25D is a top view of the shapeable waveguide assembly and highlights a distal portion. The fiber optic bundle 2514 is positioned in sleeve 2520 which is coupled with the proximal end of the optical waveguide 2522 thereby allowing light to be delivered from the light source to the waveguide. The flat planar arrangement of the fiber optic bundle 2514 allows the waveguide to be efficiently filled with light from the proximal end thereof. The fibers in the bundle may be potted and polished in the sleeve. The waveguide is preferably a non-fiber optic optical waveguide that has been injection molded of a polymer such as cyclo olefin polymer or copolymer. Thus, the optical waveguide is a single waveguide and also is preferably formed of a single, homogenous material. The optical waveguide 2522 is cradled in a holding frame 2530 that is also coupled to a distal portion of the malleable backing 2516. The optical waveguide 2522 has a rectangular planar portion 2528 and also an enlarged flanged portion 2526 that fits around the holding frame 2530 to help secure it into position. This is not intended to be limiting and one of skill in the art will appreciate that the optical waveguide may have other configurations and other engagement mechanisms for securing it to the malleable backing. For example, instead of the flange extending outward from the optical waveguide, the holding frame may have a flange that engages a recessed region in the optical waveguide. The proximal end of the optical waveguide is also secured in sleeve 2520. In some embodiments, the optical waveguide may have standoffs 2523 which form an air gap between the optical waveguide and the holding frame. FIG. 25H illustrates exemplary standoffs on the optical waveguide. The air gap helps improve light transmission efficiency through the waveguide as contact between the waveguide and the holding frame would result in light loss. In other embodiments, the standoffs may be on the holding frame instead of the waveguide. In still other embodiments, the standoffs may be on both the holding frame and the waveguide.

Figure 25E:
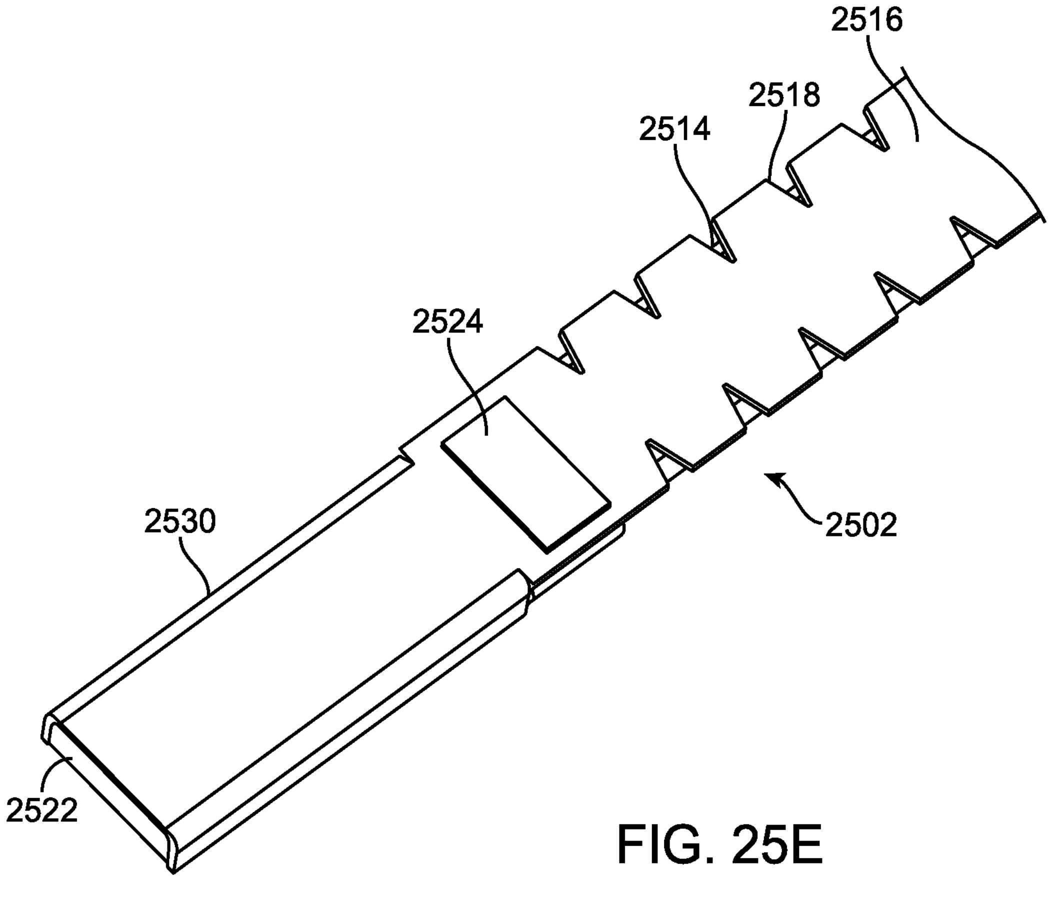

FIG. 25E illustrates a bottom perspective view and highlights a distal portion of the assembly 2502. As previously mentioned, the triangular cutouts 2518 help facilitate bending of the malleable backing. Other cutouts may be used in the malleable backing in order to facilitate bending in other directions. In the present embodiment, the cutouts form a hinge which facilitates bending the backing into a convex or concave shape. The backing may have compound bends each with different radii. Window 2524 in the backing allows a portion of the optical waveguide to protrude therethrough, thereby helping with engagement of the optical waveguide and the backing.

Figure 25F:
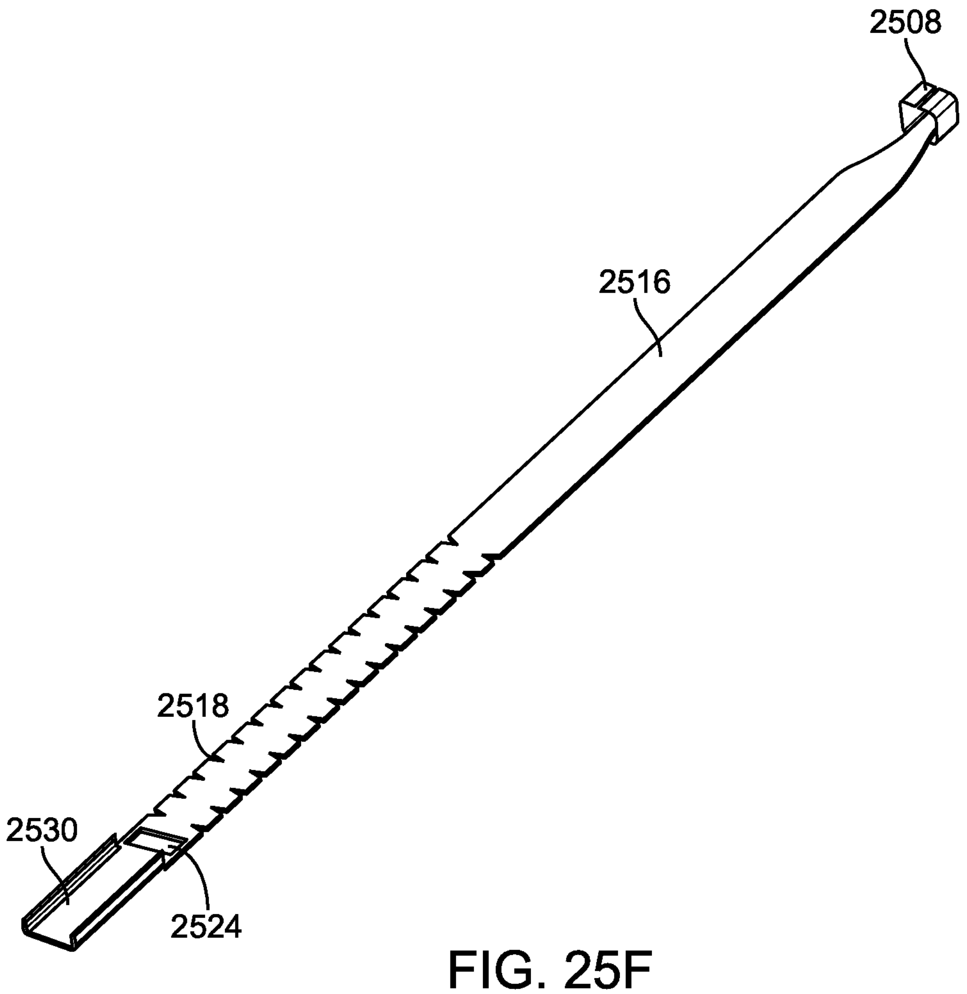
Figure 25G:
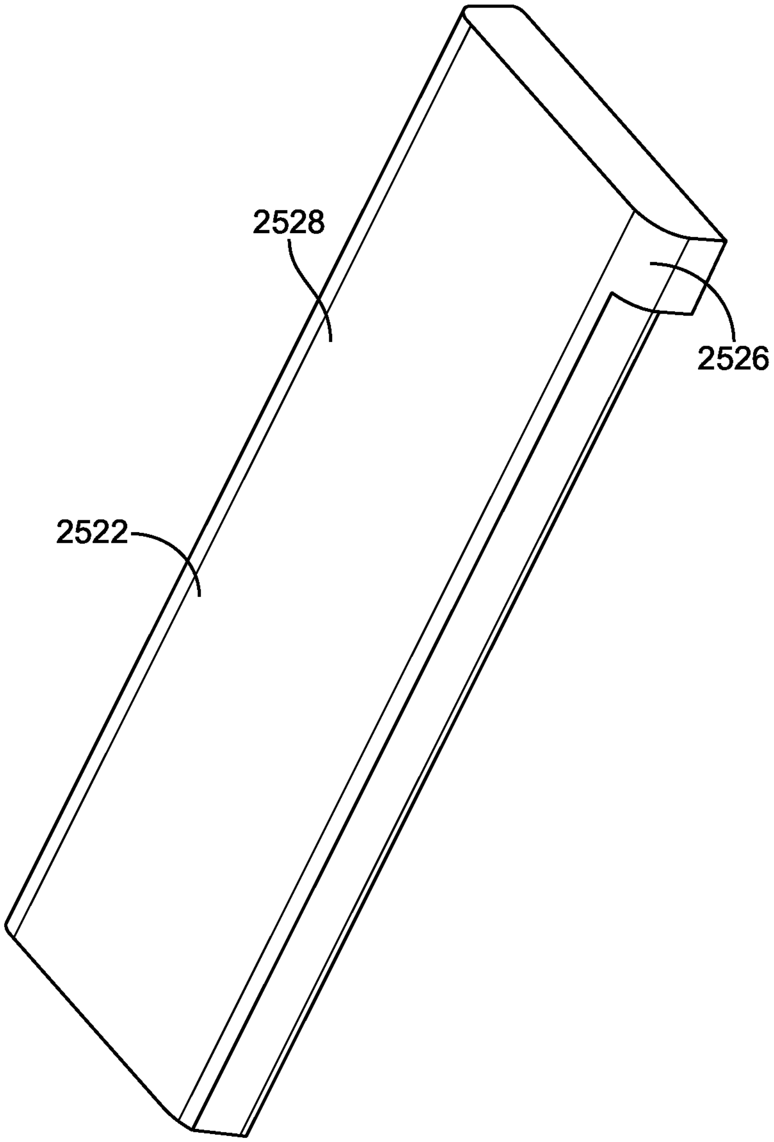
Figure 25H:
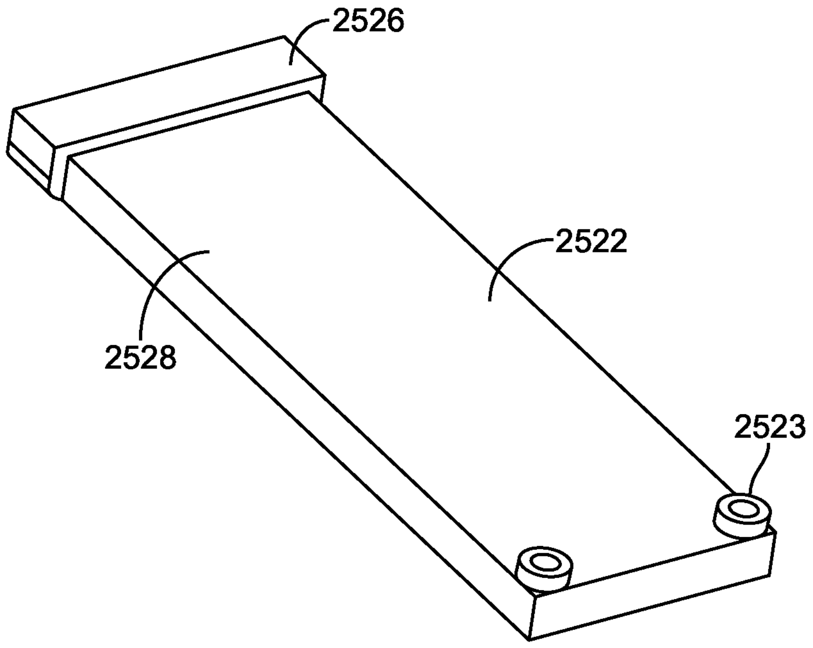

FIG. 25F illustrates a top perspective view of the malleable backing 2516 with the fiber optic bundle and optical waveguide removed. This view more clearly illustrates the flat planar proximal portion of the backing, the serrated hinge 2518 and the holding frame 2530 for the optical waveguide. The frame includes a pair of rails on either side of the frame for holding the optical waveguide. FIG. 25G illustrates the optical waveguide 2522 including the flat, rectangular portion 2528 and the flanged region 2526 for engaging with the frame. The shapeable waveguide assembly may incorporate any of the other features disclosed in this specification. For example, the optical waveguide may include any of the light extraction features described herein. The optical waveguide may also include any of the coatings, films or other optical claddings disclosed herein to enhance light transmission by total internal reflection, or to help extract light therefrom, or to control the type of light being delivered (e.g. polarizing light, diffuse light, etc.).

Figure 25I:
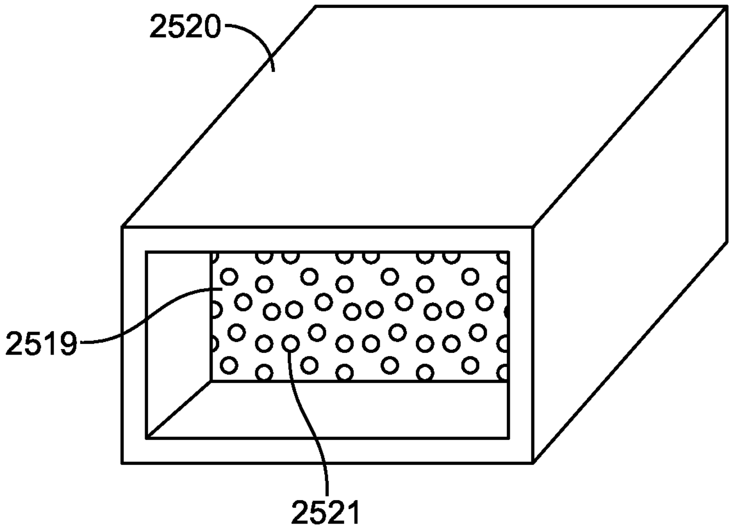

FIG. 25I illustrates the sleeve more closely. The fiber optic elements 2521 may be inserted into the sleeve from one end and then potted in place with epoxy 2519 or another material. The ends of the fibers can then be polished in the sleeve. The ends of the fibers are preferably recessed from the opposite end of the sleeve in order to form a receptacle for receiving the optical waveguide which can then butt up against the optical fibers. An index matching adhesive may then be used to attach the optical waveguide to the sleeve and optical fibers. In other embodiments, the optical fibers may be flush with the opposite end of the sleeve and the waveguide may simply butt up against the sleeve and fibers.

Coupling with Light Source

Any of the waveguides described in this specification may be coupled to a remote light source such as an external xenon lamp. The waveguide may be coupled to a fiber optic cable that is also coupled to the light source. The fiber optic cable is often a bundle of fiber optics. Preferably, the fiber bundles couple light from a source that may emit with a higher numerical aperture (NA) factor than the bundle. Many of the sources produce the numerical with a higher NA since the light source manufacturer does not always know which cable is going to be used. A simple lens and/or lens reflecting surfaces may be attached around or in front of a light source (e.g. xenon light sources, the most widely used source nowadays, are a discharge electric bulb housed in the focal point of a parabolic or other shape mirror. Many xenon light boxes have a lens in front of the bulb to effectively couple to a fiber bundle). To optimize the amount of light coupled into a cable requires consideration of several factors. One of which is matching the NA of the light source to the cable. As mentioned earlier, this may be achieved by placing an optical component between the bulb and the cable that matches the NA. Another important factor is the design of the fiber bundle. Several variables to consider when designing a bundle include:

A) the packing ratio and arrangement of individual fibers in the bundle;

B) the core to cladding ratio in the fiber bundle; and

C) Fresnel loss and misalignment losses.

Packing Ratio

Figure 26:
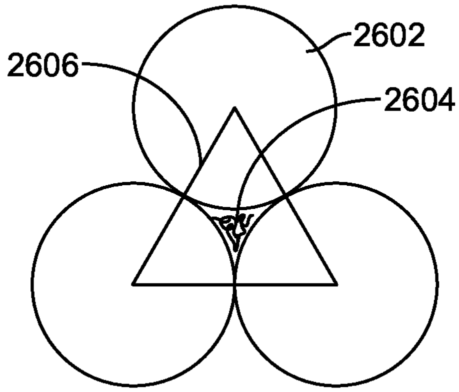
FIG. 26 illustrates packing of fibers in a triangular pattern.

Many fibers are produced round. When assembled into a bundle, there is a dead space between the individual round elements, especially when there are disruptions in the bundle which yields poorly packed bundle and transmission. By taking the best case scenario, packing fibers in a triangular pattern as seen in FIG. 26 allows us to achieve the smallest possible dead space. This dead space may be calculated by dead space 2604 divided by the area 2606 of the triangle created by the fibers based on their center point. In the exemplary embodiment in FIG. 26, this ratio is 90.7% which means that 9.3% of the area is lost between circular fibers. The loss from packing fibers on an infinite space or a very high count of fibers will result in filling of about 9.3% or higher.

Figure 27:
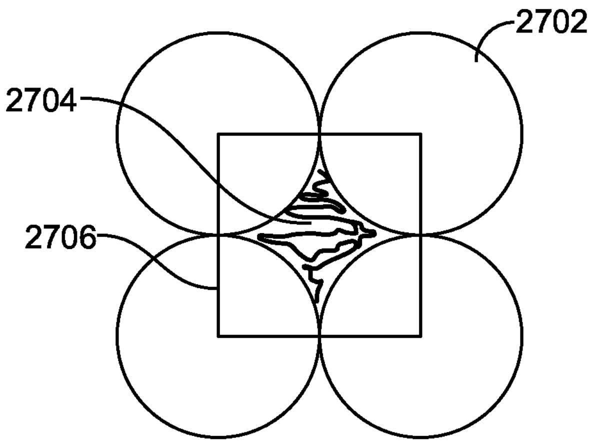
FIG. 27 illustrates packing of fibers in a square pattern.

Now comparing this to fibers 2702 that are stacked in a square pattern as seen in FIG. 27, we can calculate that the ratio of the dead area 2704 divided by the area of the square 2706 defined by the center points of the fibers 2702 is 78.5%. This means that 21.5% of area between the circles is lost. This calculation is summarized below and is based on an infinite number of fibers. Therefore packing the fibers in a triangular pattern is the optimal configuration for minimizing dead area between fibers.

The dead area in triangular packing=difference between triangle area $[(2r)^2\sqrt{}/3]/3$ and the area of half a circle is $(\pi r^2)/2$. Therefore the dead area=$[\sqrt{3}+\pi/2]r^2$, which is reduced to 0.16125 $r^2$ where r is the radius of the fibers. For square packing the dead area is estimated as the difference between the square area ($2r^2$) and the area of the circle $\pi r^2$. Thus the dead area for square packing is $(4-\pi)\ r^2=0.85841r^2$, much larger than for the triangular packing.

Cladding Area

Fibers are not able to guide light on its core (the body of the fiber) unless they have cladding (or a coat over the core) with a lower refractive index than the core itself. Although the cladding is often made from transparent material, the light is not guided and it is lost. Traditional illumination fibers used in medical applications are produced from glass, with a 55 μm diameter and a 50 μm core. Computing the area difference of two circles of mentioned diameters leads to a 17.4% loss from cladding area that each fiber has. This can be minimized by identifying a fiber that has the highest possible core to cladding ratio.

Fresnel Loss and Misalignment

Glass fibers have an approximate refractive index equal to 1.5. The discontinuity of refractive index when light goes from air to fiber or fiber to air is responsible for approximately 4% loss (called Fresnel loss) at each interface, totaling 8%. When one fiber is to be connected to another bundle, in addition to Fresnel losses, we also get losses from misalignment. That is if the fibers are misaligned in the longitudinal direction by as much as 0.5 mm, one can approximate the losses to be up to 10%.

By adding the losses stated above, based on the best case scenario for the total loss, would add up to (9.3%+17.4%+8%+10%)=44.7% of the total light. This is a best approximation of loss that a bundled fiber cable (made from 50 μm/55 μm core/cladding glass fibers). Therefore a glass bundle would not be able to transmit higher than 55.3% of the input light.

By changing the fibers from glass to plastic in exemplary embodiments, we can change the cladding area loss. A 750 μm plastic fiber (commercially available and flexible enough to bend to necessary curvatures) has a 735 μm more and 15 μm cladding. The change in cladding area reduces the loss from 17.4% to 3.96% loss by reducing unusable transmitting area on the fibers. Other fibers such as 1000 μm core, or 1500 μm, 2000 μm, 2500 μm or 3000 μm diameter are available and may be used to construct fiber bundles. Use of the 750 μm fibers is discussed below.

Calculating the total loss for 750 μm is straight forward, by changing the area ratio of core and cladding to total area and leaving other sources of loss unchanged, the total loss is estimated to be 9.3%+3.96%+8%+10%=31.3%. Thus transmission should be up to 68.7%. This is the biggest gain that can be achieved by switching from the glass 50 μm/55 μm fibers previously described to the plastic 750 μm/735 μm plastic fibers describe above. Performing the same calculation for a 250 μm plastic fiber with a core diameter of 240 μm and outer diameter of 250 μm, the lost area is estimated to be 7.8% vs 3.96% of the 750 μm fiber. Thus, the 750 μm plastic fiber provides desired efficiency and this also helps to keep the illumination system thermally cool.

Next, the effect of finite size bundles is examined along with designs that maximize transmission of light along a bundled cable. The first goal is to determine the best packing scheme. As mentioned earlier, since most fibers are round, there are various ways to stack the bundle. The goal is to minimize the interstitial space (IS). By minimizing the space, system efficiency increases since less light is lost between the fibers.

Figure 28:
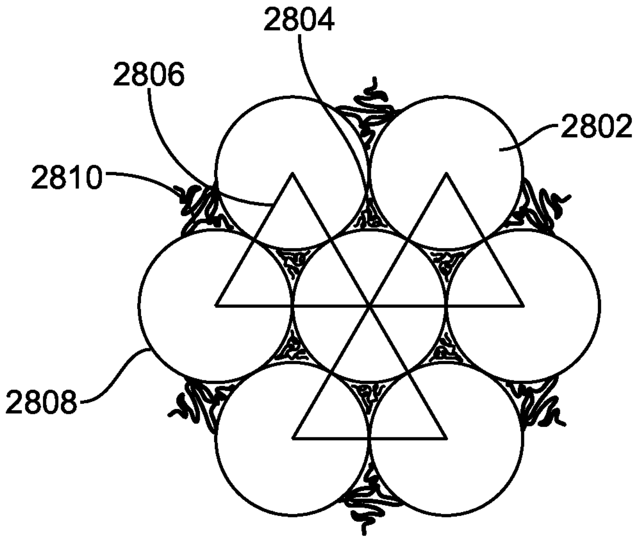
FIG. 28 illustrates a fiber bundle approximately a circle.

Presented below are several examples of stacking the fibers and calculating the interstitial space. The optimal arrangement places the fibers in a triangular pattern. Additionally, it would also be desirable to make an arrangement of fibers in a bundle as close to a circular shape as possible, therefore in FIG. 28, seven fibers 2802 are arranged in triangular patterns 2806 to minimize interstitial space, and the triangles are then arranged into a hexagon 2808 in order to approximate a circle. The interstitial space may be estimated as six times the enclosed interstitial space 2804, plus six times the unenclosed interstitial space 2810 divided by two. The dead space 2804 is also illustrated between fibers. The fibers form three rows with two rows containing two fibers and a row of three fibers in between the other two rows.

Figure 29B:
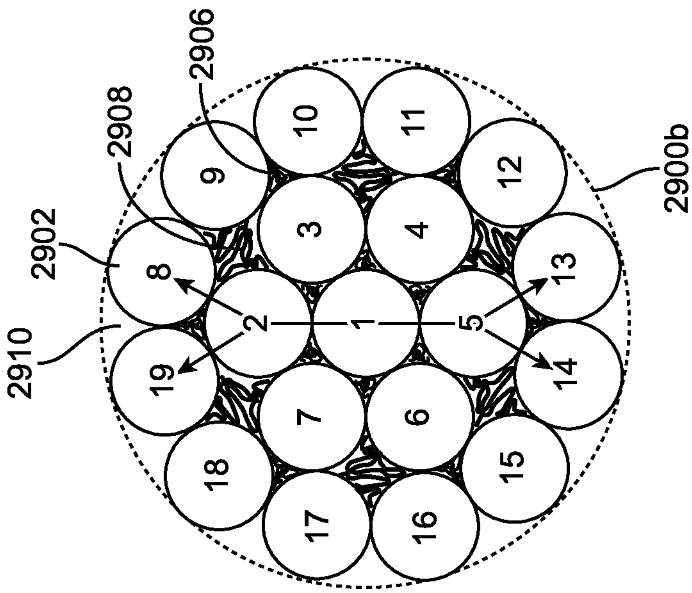
FIGS. 29A-29B illustrate another exemplary embodiment a fiber bundle.
Figure 29A:
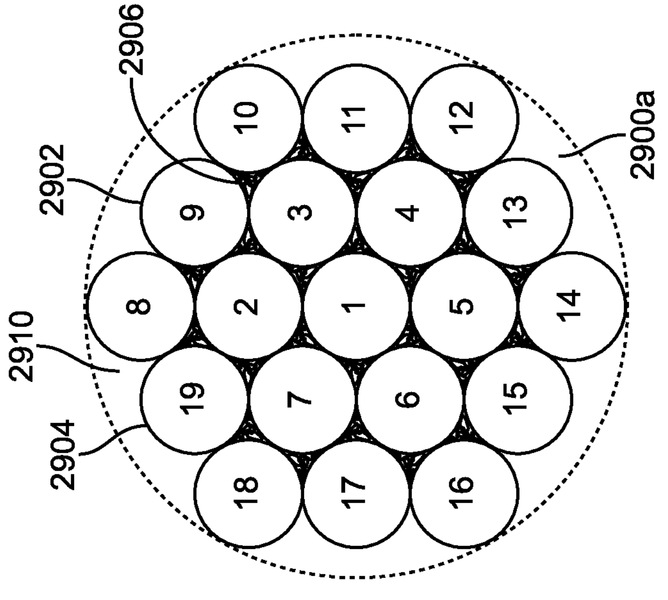

FIGS. 29A-29B illustrate another exemplary embodiment of fiber bundle packing, each having three layers of concentric equal diameter fibers. The dotted line around each fiber bundle is the same diameter and has a circumference of 3.75 mm when 750 μm diameter fibers are used.

In FIG. 29A, nineteen fibers 2902 are packed together to form a hexagon 2904 that approximates a circular bundle 29000*a*. The interstitial spaces include interstitial space 2906 disposed between fibers which is a triangular shaped region, as well as a half diamond-like interstitial space 2910 around the outer perimeter of the bundle. This embodiment is similar to the previous embodiment except that an additional layer of fibers is packed around the previous embodiment. This configuration is more closely packed than the embodiment in FIG. 29B where the nineteen fibers 2902 are packed to form dodecahedron bundle 2900*b* with two geometries of interstitial space, the same triangular interstitial space 2906 as in FIG. 29A, and a diamond-like interstitial space 2908, as well as the half diamond-like interstitial spaces 2910 around the outer perimeter of the bundle. The diamond-like space 2908 is double the area of the half diamond-like space 2910 in hexagonal embodiment. Unlike the embodiment of FIG. 29A where the fibers are in linear rows, the fibers in FIG. 29B are in a shifted annular arrangement that leads to a closer contour to a circle.

For the hexagonal arrangement in FIG. 29A, the total interstitial space is equal to 24 interstitial spaces 2906 plus 12 half-diamond spaces 2910, or 6 diamond spaces 2906. A calculation of this space estimates it to be $64.53r^2$ units of area. For the dodecahedron, the interstitial space is equal to twelve of the triangular interstitial spaces 2906 plus six diamond-like spaces 2908 and also twelve half diamond-like spaces 2910 or six diamond-like spaces 2908. The total space is calculated to be $67.74r^2$ units of area. Thus, the ratio of the hexagonal packing to the dodecahedron packing is 95.26% which means that the hexagonal arrangement has about 4.74% less interstitial space than the dodecahedron shape, and hence it is more efficient.

Figure 30B:
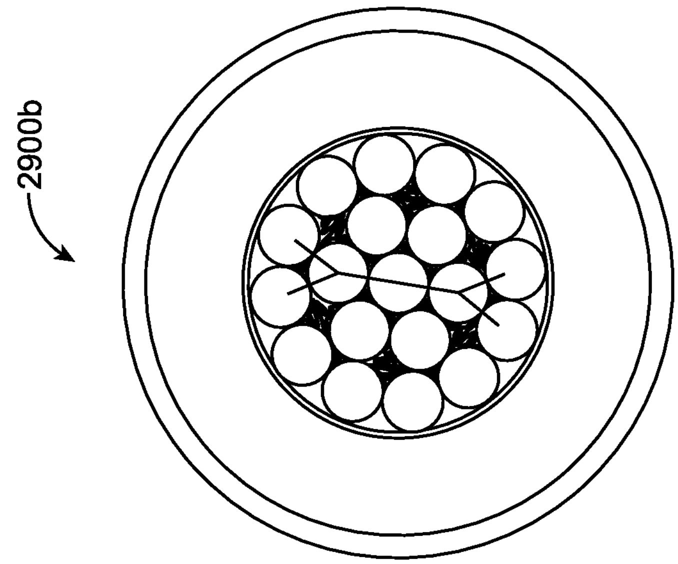
FIGS. 30A-30B further illustrate the embodiments of FIGS. 29A-29B.
Figure 30A:
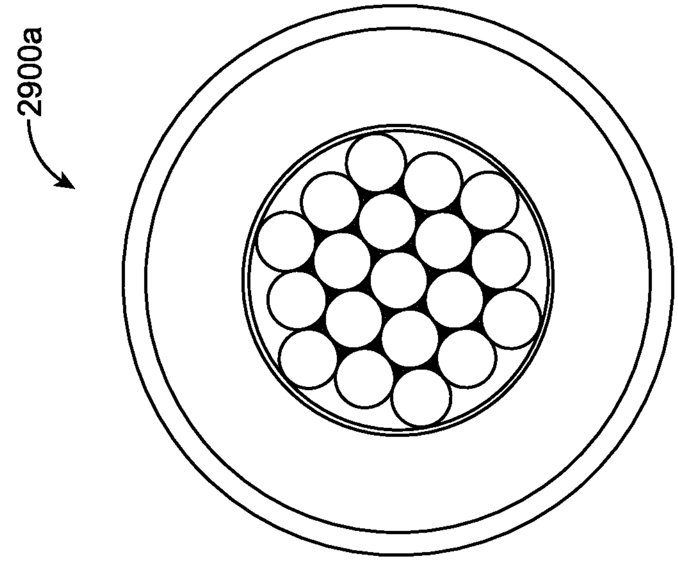

FIG. 30A illustrates the hexagonal fiber bundle of FIG. 29A above. FIG. 30B illustrates the dodecahedral fiber bundle of FIG. 29B above. Bothe embodiments have the same diameter fibers, and the same outer diameter of the bundle when estimated as a circle. Some dislocation from a perfect hexagon are noticed in FIG. 30A due to the large size of the ferrule holding the fibers and thus it would be preferably to use a hexagonal containment barrier since otherwise, the fibers will not be able to hold a perfect hexagonal shape when surrounded by a circular wall.

The embodiments described above employ plastic large core fibers with desirable ratios of core to cladding. Preferably a large core is used with thin cladding. This helps the fibers transmit light efficiently from an external light source to the waveguide. Efficiency is desirable since it helps keep temperature of the system low. Glass fibers are less desirable since they are expensive and are thus cost prohibitive in a disposable cable while the plastic is efficient and much less expensive. However, glass fibers may be used in any of the embodiments such as an exemplary glass fiber having a diameter of about 250 μm.

In still other embodiments, the fiber bundle may be heated and compressed to decrease or eliminate the interstitial space, further increasing efficiency. For example, the hexagonally shaped fiber bundle may be heated and compressed to form a hexagonal bundle with little or no interstial space, and the individual fibers will be reshaped into approximately hexagonally shaped fibers.

Figure 31:
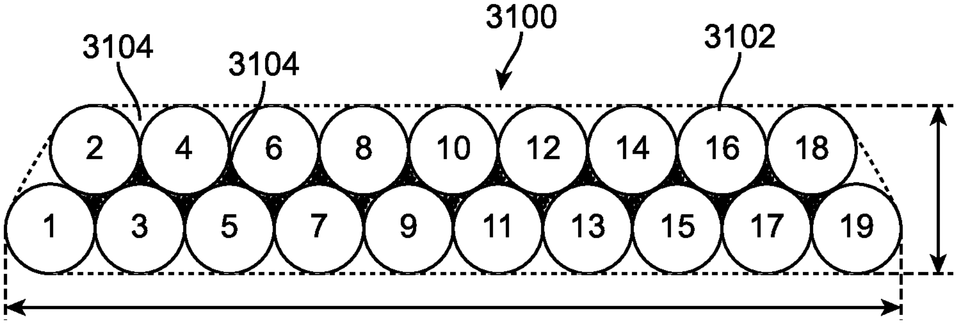
FIG. 31 illustrates a flat fiber bundle.

Previous embodiments of fiber bundles were circular. In some circumstances it would be desirable to provide a fiber bundle that is flat. FIG. 31 illustrates a flat fiber bundle 3100 having 19 fibers 3102 with triangular shaped interstitial spaces 3104 between the fibers and along the perimeter, thereby forming a ribbon cable with a low profile. The 19 fibers 3102 are compatible with the 3.5 mm diameter bundle previously described above, but have a different form factor.

A single row of fibers may also be attractive as a very flat ribbon cable. Including the advantage that if properly wrapped, it could be contoured to any shape, such as a ring or bent. But for wider lengths, such as a length of 14.25 mm, the ribbon cable may be too wide to be practical. Therefore the two row device in FIG. 31 when arranged symmetrically leads to a D shaped ribbon cable as indicated by the dotted line. The length of the base of the cable may estimated as 10 times the diameter of the fibers, which in this embodiment is 7.5 mm, and the height is estimated at $(2+\sqrt{3})r=3.732r=1.3995$ mm in this embodiment.

Figure 32:
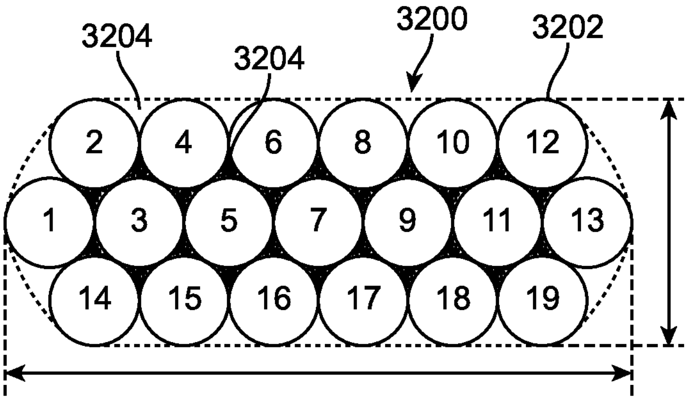
FIG. 32 illustrates another flat fiber bundle.

An alternative embodiment of a flat ribbon cable 3200 is illustrated in FIG. 32 with three rows of fibers 3202 packed symmetrically and separated by interstitial spaces 3204 internally and along the outer perimeter of the cable. The height is estimated as $5.575r=2.09$ mm, and the length of the base is estimated to be 7 times the diameter of the fibers, or 5.25 mm. Adding a fourth layer for a 19 fiber cable is close to the hexagonal arrangement and lacks symmetry which is desirable since this structure provides more mechanical stability to the bundle.

Any of the fiber bundles described herein may be coupled to another fiber, fiber bundle or waveguide by butt coupling the two together or there may be optics disposed in between the two to correct misalignment errors. Additionally, coupling gels, lenses, relay rods or hollow coated cones may also be used to join the two together. Also, in any embodiment, the fibers may be formed from a polymer such as any optical plastic, or they may be formed from glass. Any embodiment may have smaller size or different shaped fibers inserted into the interstitial space formed during packing of the round fibers. The smaller size fiber may be shaped to fit the interstitial space and thus may be triangular or diamond-like in shape.

Figure 33:
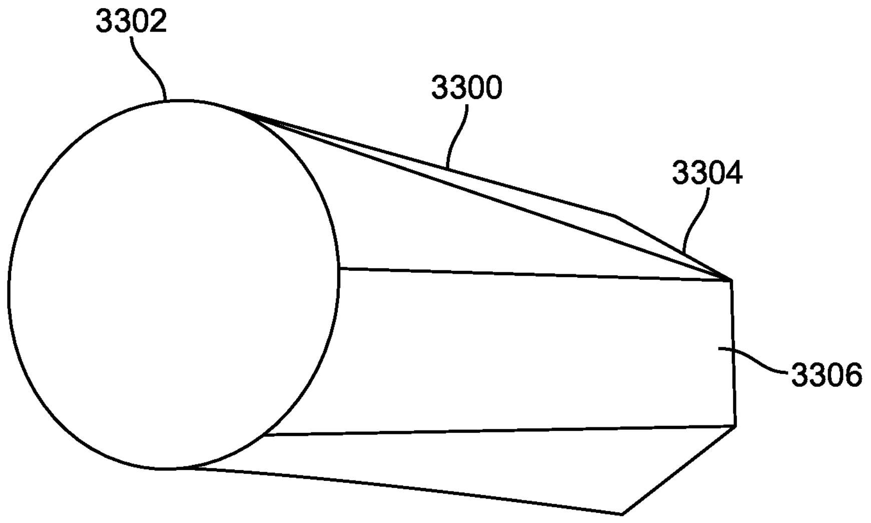
FIG. 33 illustrates an exemplary coupler.

Even coupling a round to hexagonal bundle may be achieved with the exemplary coupler 3300 illustrated in FIG. 33. The coupler 3300 has a round end 3302 on one end of the coupler, and the outer surface has a plurality of facets 3306 which transition the round end into a hexagonal end 3304, thereby allowing coupling of two different shaped fiber bundles. Oversizing either or both ends is advantageous since it reduces misalignment errors between the two bundles.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A shapeable illuminated surgical instrument, comprising:
- an optical connector configured to couple to a light source;
- a fiber optic bundle having a proximal region and a distal region, wherein the fiber optic bundle is configured to receive light from the optical connector at the proximal region and transmit the light from the proximal region to the distal region, wherein the fiber optic bundle is cylindrically shaped in the proximal region, and wherein the fiber optical bundle is flat and planar in the distal region;
- a malleable backing element extending along the distal region of the fiber optic bundle, wherein the malleable backing element is configured to (i) undergo plastic deformation in response to a bending force to thereby adjust the distal region of the fiber optic bundle from a first shape to a second shape, and (ii) maintain the distal region of the fiber optic bundle in the second shape after the bending force ceases, as a result of the plastic deformation of the malleable backing element; and
- a crimping element crimped around the fiber optic bundle thereby coupling the fiber optic bundle to the malleable backing element.

2. The shapeable illuminated surgical instrument of claim 1, further comprising a waveguide optically coupled to the distal region of the fiber optic bundle, wherein the waveguide comprises a front surface configured to emit the light and a rear surface opposite the front surface.

3. The shapeable illuminated surgical instrument of claim 2, wherein the waveguide comprises a plurality of waveguides that are encapsulated in a flexible layer of material.

4. The shapeable illuminated surgical instrument of claim 3, wherein each waveguide is optically coupled with a respective optical fiber of the fiber optic bundle.

5. The shapeable illuminated surgical instrument of claim 3, wherein the plurality of waveguides are coupled to a substrate.

6. The shapeable illuminated surgical instrument of claim 5, wherein the substrate is an adhesive.

7. The shapeable illuminated surgical instrument of claim 5, wherein the substrate is a film.

8. The shapeable illuminated surgical instrument of claim 2, further comprising a cladding disposed over the rear surface.

9. The shapeable illuminated surgical instrument of claim 2, wherein the malleable backing element is coupled to the waveguide with the malleable backing element extending along the rear surface of the waveguide.

10. The shapeable illuminated surgical instrument of claim 2, wherein the waveguide has a longitudinal axis, and wherein the waveguide comprises a plurality of control elements that extend transverse to the longitudinal axis, wherein the plurality of control elements are configured to extract the light from the waveguide.

11. The shapeable illuminated surgical instrument of claim 1, wherein the fiber optic bundle further comprises a flaring portion between the proximal region and the distal region.

12. The shapeable illuminated surgical instrument of claim 1, further comprising a strain relief disposed over the proximal region of the fiber optic bundle, wherein the strain relief is configured to reduce kinking of the fiber optic bundle.

13. A surgical system, comprising:
- a surgical retractor; and
- a shapeable illuminated surgical instrument coupled to the surgical retractor, wherein the shapeable illuminated surgical instrument comprises:
  - an optical connector configured to couple to a light source,
  - a fiber optic bundle having a proximal region and a distal region, wherein the fiber optic bundle is configured to receive light from the optical connector at the proximal region and transmit the light from the proximal region to the distal region, wherein the fiber optic bundle is cylindrically shaped in the proximal region, and wherein the fiber optical bundle is flat and planar in the distal region,
  - a malleable backing element extending along the distal region of the fiber optic bundle, wherein the malleable backing element is configured to (i) undergo plastic deformation in response to a bending force to thereby adjust the distal region of the fiber optic bundle from a first shape to a second shape, and (ii) maintain the distal region of the fiber optic bundle in the second shape after the bending force ceases, as a result of the plastic deformation of the malleable backing element, and wherein the malleable backing element is shapeable to conform to a surface of the surgical retractor;
  - a waveguide optically coupled to the distal region of the fiber optic bundle; and
  - a sleeve disposed over at least the distal region of the fiber optic bundle and the waveguide.

14. The surgical system of claim 13, wherein the waveguide comprises a front surface configured to emit the light and a rear surface opposite the front surface.

15. The surgical system of claim 14, wherein the waveguide comprises a plurality of waveguides that are encapsulated in a flexible layer of material.

16. The surgical system of claim 15, wherein each waveguide is optically coupled with a respective optical fiber of the fiber optic bundle.

17. The surgical system of claim 15, wherein the plurality of waveguides are coupled to a substrate.

18. The surgical system of claim 17, wherein the substrate is an adhesive.

19. The surgical system of claim 17, wherein the substrate is a film.

20. The surgical system of claim 14, further comprising a cladding disposed over the rear surface.

21. The surgical system of claim 14, wherein the malleable backing element is coupled to the waveguide with the malleable backing element extending along the rear surface of the waveguide.

22. The surgical system of claim 14, wherein the waveguide has a longitudinal axis, and wherein the waveguide comprises a plurality of control elements that extend transverse to the longitudinal axis, wherein the plurality of control elements are configured to extract the light from the waveguide.

23. The surgical system of claim 13, wherein the fiber optic bundle further comprises a flaring portion between the proximal region and the distal region.

24. The surgical system of claim 13, further comprising:

a strain relief disposed over the proximal region of the fiber optic bundle, wherein the strain relief is configured to reduce kinking of the fiber optic bundle; and a crimping element crimped around the fiber optic bundle thereby coupling the fiber optic bundle to the malleable backing element.

* * * * *